US009872920B2

(12) United States Patent
Chang et al.

(10) Patent No.: US 9,872,920 B2
(45) Date of Patent: *Jan. 23, 2018

(54) PEGYLATION BY THE DOCK AND LOCK (DNL) TECHNIQUE

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US); William J. McBride, Boonton, NJ (US); Edmund A. Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/247,386

(22) Filed: Aug. 25, 2016

(65) Prior Publication Data

US 2016/0361435 A1  Dec. 15, 2016

Related U.S. Application Data

(60) Division of application No. 13/589,575, filed on Aug. 20, 2012, now Pat. No. 9,457,100, which is a division of application No. 13/150,613, filed on Jun. 1, 2011, now Pat. No. 8,277,817, which is a division of application No. 12/644,146, filed on Dec. 22, 2009, now Pat. No. 7,981,398, which is a division of application No. 11/925,408, filed on Oct. 26, 2007, now Pat. No. 7,666,400, which is a continuation-in-part of application No. 11/391,584, filed on Mar. 28, 2006, now Pat. No. 7,521,056, said application No. 11/925,408 is a continuation-in-part of application No. 11/478,021, filed on Jun. 29, 2006, now Pat. No. 7,534,866, said application No. 11/925,408 is a continuation-in-part of application No. 11/633,729, filed on Dec. 5, 2006, now Pat. No. 7,527,787, which is a continuation-in-part of application No. PCT/US2006/010762, filed on Mar. 24, 2006, and a continuation-in-part of application No. PCT/US2006/012084, filed on Mar. 29, 2006, and a continuation-in-part of application No.

(Continued)

(51) Int. Cl.
| | |
|---|---|
| A61K 47/48 | (2006.01) |
| A61K 38/18 | (2006.01) |
| A61K 38/19 | (2006.01) |
| A61K 38/21 | (2006.01) |
| A61K 51/10 | (2006.01) |
| B82Y 5/00 | (2011.01) |
| B82Y 10/00 | (2011.01) |

(52) U.S. Cl.
CPC .... *A61K 47/48338* (2013.01); *A61K 38/1816* (2013.01); *A61K 38/193* (2013.01); *A61K 38/212* (2013.01); *A61K 47/48215* (2013.01); *A61K 47/48507* (2013.01); *A61K 47/48576* (2013.01); *A61K 51/1048* (2013.01); *B82Y 5/00* (2013.01); *B82Y 10/00* (2013.01); *C07K 2319/00* (2013.01); *C07K 2319/70* (2013.01)

(58) Field of Classification Search
CPC .... A61K 47/60; A61K 38/1816; A61K 38/19; A61K 38/391; A61K 38/193; A61K 38/21; A61K 38/212; A61K 38/215; A61K 38/219; A61K 38/217; A61K 47/6883; A61K 51/10; B82Y 5/00; B82Y 10/00; C07K 16/00; C07K 2319/70; C07K 2319/73
See application file for complete search history.

(56) References Cited

U.S. PATENT DOCUMENTS

| 4,046,722 A | 9/1977 | Rowland |
|---|---|---|
| 4,699,784 A | 10/1987 | Shih et al. |

(Continued)

FOREIGN PATENT DOCUMENTS

| WO | 2000/068248 | 11/2000 |
|---|---|---|
| WO | 2006/107617 | 10/2006 |

(Continued)

OTHER PUBLICATIONS

Roberts et al., Advanced Drug Delivery Reviews 54: 459-476, 2002.*
Axtell et al., "Interferon-β exacerbates Th17-mediated inflammatory disease", Trends Immunol. Jun. 2011;32 6):272-7.
Azizi et al., "The potential role of angiogenic factors in rheumatoid arthritis", Int J Rheum Dis. May 2014;17(4):369-83.
Bruno et al., "The advent of monoclonal antibodies in the treatment of chronic autoimmune diseases", Neural Sci. Jul. 2011;31 Suppl 3:283-8.
Cardillo et al., "Targeting both IGF-1R and mTOR synergistically inhibits growth of renal cell carcinoma in vitro", BMC Cancer. Apr. 1, 2013;13:170.

(Continued)

Primary Examiner — Phuong Huynh
(74) Attorney, Agent, or Firm — Richard A. Nakashima

(57) ABSTRACT

The present invention concerns methods and compositions for forming PEGylated complexes of defined stoichiometry and structure. In preferred embodiments, the PEGylated complex is formed using dock-and-lock technology, by attaching a target agent to a DDD sequence and attaching a PEG moiety to an AD sequence and allowing the DDD sequence to bind to the AD sequence in a 2:1 stoichiometry, to form PEGylated complexes with two target agents and one PEG moiety. In alternative embodiments, the target agent may be attached to the AD sequence and the PEG to the DDD sequence to form PEGylated complexes with two PEG moieties and one target agent. In more preferred embodiments, the target agent may comprise any peptide or protein of physiologic or therapeutic activity. The PEGylated complexes exhibit a significantly slower rate of clearance when injected into a subject and are of use for treatment of a wide variety of diseases.

13 Claims, 18 Drawing Sheets

Related U.S. Application Data

PCT/US2006/025499, filed on Jun. 29, 2006, and a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, and a continuation-in-part of application No. 11/478,021, filed on Jun. 29, 2006, now Pat. No. 7,534,866.

(60) Provisional application No. 60/668,603, filed on Apr. 6, 2005, provisional application No. 60/751,196, filed on Dec. 16, 2005, provisional application No. 60/782,332, filed on Mar. 14, 2006, provisional application No. 60/864,530, filed on Nov. 6, 2006.

(56) References Cited

U.S. PATENT DOCUMENTS

| | | | |
|---|---|---|---|
| 4,868,109 | A | 9/1989 | Lansdorp et al. |
| 5,770,198 | A | 6/1998 | Coller et al. |
| 5,871,945 | A | 2/1999 | Lockerbie et al. |
| 6,077,939 | A * | 6/2000 | Wei .............. A61K 47/48215 530/300 |
| 6,261,537 | B1 | 7/2001 | Klaveness et al. |
| 6,306,393 | B1 | 10/2001 | Goldenberg et al. |
| 6,524,854 | B1 | 2/2003 | Monia et al. |
| 6,617,135 | B1 | 9/2003 | Gillies et al. |
| 7,060,506 | B2 | 6/2006 | Craig |
| 7,151,164 | B2 | 12/2006 | Hansen et al. |
| 7,521,056 | B2 | 4/2009 | Chang et al. |
| 7,527,787 | B2 | 5/2009 | Chang et al. |
| 7,534,866 | B2 | 5/2009 | Chang et al. |
| 7,541,440 | B2 | 6/2009 | Goldenberg et al. |
| 7,550,143 | B2 | 6/2009 | Chang et al. |
| 7,666,400 | B2 * | 2/2010 | Chang .............. A61K 38/1816 424/134.1 |
| 7,858,070 | B2 | 12/2010 | Chang et al. |
| 7,871,622 | B2 | 1/2011 | Chang et al. |
| 7,901,680 | B2 | 3/2011 | Chang et al. |
| 7,906,121 | B2 | 3/2011 | Chang et al. |
| 7,981,398 | B2 | 7/2011 | Chang et al. |
| 8,003,111 | B2 * | 8/2011 | Chang .............. A61K 39/395 424/192.1 |
| 8,034,352 | B2 | 10/2011 | Chang et al. |
| 8,158,129 | B2 | 4/2012 | Chang et al. |
| 8,163,291 | B2 | 4/2012 | Chang et al. |
| 8,211,440 | B2 | 7/2012 | Chang et al. |
| 8,246,960 | B2 | 8/2012 | Chang et al. |
| 8,277,817 | B2 | 10/2012 | Chang et al. |
| 8,282,934 | B2 | 10/2012 | Chang et al. |
| 8,349,332 | B2 | 1/2013 | Chang et al. |
| 8,435,540 | B2 | 5/2013 | Chang et al. |
| 8,475,794 | B2 | 7/2013 | Chang et al. |
| 8,481,041 | B2 | 7/2013 | Chang et al. |
| 8,491,914 | B2 | 7/2013 | Chang et al. |
| 8,551,480 | B2 | 10/2013 | Chang et al. |
| 8,562,988 | B2 | 10/2013 | Chang et al. |
| 8,597,659 | B2 | 12/2013 | Chang et al. |
| 2003/0198956 | A1 | 10/2003 | Makowski et al. |
| 2003/0232420 | A1 | 12/2003 | Braun et al. |
| 2004/0018587 | A1 | 1/2004 | Makowski et al. |
| 2004/0126361 | A1 * | 7/2004 | Saifer .............. A61K 38/215 424/85.6 |
| 2005/0003403 | A1 | 1/2005 | Rossi et al. |
| 2006/0210475 | A1 | 9/2006 | Goldenberg et al. |
| 2006/0228300 | A1 * | 10/2006 | Chang .............. A61K 39/395 424/1.49 |
| 2007/0020259 | A1 | 1/2007 | Hansen et al. |
| 2007/0086942 | A1 | 4/2007 | Chang et al. |
| 2007/0140966 | A1 | 6/2007 | Chang et al. |
| 2009/0060862 | A1 | 3/2009 | Chang et al. |
| 2009/0111143 | A1 | 4/2009 | Goldenberg et al. |
| 2009/0304580 | A1 | 12/2009 | Goldenberg et al. |
| 2010/0068137 | A1 | 3/2010 | Chang et al. |
| 2010/0189641 | A1 | 7/2010 | Chang et al. |
| 2010/0189689 | A1 | 7/2010 | Chang et al. |
| 2010/0233779 | A1 | 9/2010 | Govindan et al. |
| 2010/0261885 | A1 | 10/2010 | Chang et al. |
| 2011/0020273 | A1 | 1/2011 | Chang et al. |
| 2011/0064754 | A1 | 3/2011 | Taylor et al. |
| 2011/0143417 | A1 | 6/2011 | Chang et al. |
| 2011/0158905 | A1 | 6/2011 | Goldenberg et al. |
| 2011/0189083 | A1 | 8/2011 | Chang et al. |
| 2011/0300105 | A1 | 12/2011 | Chang et al. |
| 2012/0093769 | A1 | 4/2012 | Chang et al. |
| 2012/0196346 | A1 | 8/2012 | Chang et al. |
| 2012/0276100 | A1 | 11/2012 | Chang et al. |
| 2012/0276608 | A1 | 11/2012 | Chang et al. |
| 2013/0078183 | A1 | 3/2013 | Chang et al. |
| 2013/0109073 | A1 | 5/2013 | Chang et al. |
| 2013/0164816 | A1 | 6/2013 | Chang et al. |
| 2013/0217091 | A1 | 8/2013 | Chang et al. |
| 2013/0295005 | A1 | 11/2013 | Chang et al. |

FOREIGN PATENT DOCUMENTS

| | | | |
|---|---|---|---|
| WO | 2006/107786 | | 10/2006 |
| WO | 2007/075270 | | 7/2007 |
| WO | 2008/033413 | | 3/2008 |
| WO | WO2009/055653 | * | 4/2009 |

OTHER PUBLICATIONS

Chang et al., "The dock and lock method: a novel platform technology for building multivalent, multifunctional structures of defined composition with retained bioactivity", Clin Cancer Res. Sep. 15, 2007;13(18 Pt 2):5586s-5591s.

Chang et al., "A new method to produce monoPEGylated dimeric cytokines shown with human interferon-α2b", Bioconjug Chem. Oct. 21, 2009;20(10):1899-907.

Chang et al., "A novel class of anti-HIV agents with multiple copies of enfuvirtide enhances inhibition of viral replication and cellular transmission in vitro", PLoS One. 2012;7(7):e41235.

Chang et al., "Evaluation of a novel hexavalent humanized anti-IGF-1R antibody and its bivalent parental IgG in diverse cancer cell lines", PLoS One. 2012;7(8):e44235.

Goldenberg et al., "Cancer Imaging and Therapy with Bispecific Antibody Pretargeting", Update Cancer Ther. Mar. 2007;2(1):19-31.

Govindan et al., "Designing immunoconjugates for cancer therapy", Expert Opin Biol Ther. Jul. 2012;12(7):873-90.

Helliwell et al., "Monoclonal antibodies in multiple sclerosis treatment: current and future steps", Ther Adv Neural Disord. Jul. 2009;2(4):195-203.

Hron et al., "Type I IFN protects against murine lupus", J Immunol. Aug. 1, 2004;173(3):2134-42.

Hsu et al., "Interleukin-19 blockade attenuates collagen-induced arthritis in rats", Rheumatology (Oxford). Mar. 2012;51(3):434-42.

Ionescu et al., "Prolonged treatment with interferon alpha and peginterferon induces rheumatoid arthritis syndrome and erythema nodosum", J Gastrointestin Liver Dis. Jun. 2008;17(2):211-2.

Kuerten et al., "MP4- and MOG:35-55-induced EAE in C57BL/6 mice differentially targets brain, spinal cord and cerebellum", J Neuroimmunol. Sep. 2007;189(1-2):31-40.

Lipiainen et al., "Formulation and stability of cytokine therapeutics", J Pharm Sci. Feb. 2015;104(2):307-26.

Liu et al., "Trop-2-targeting tetrakis-ranpimase has potent antitumor activity against triple-negative breast cancer", Mol Cancer. Mar. 10, 2014;13:53.

McFarland et al., "Determinant spreading associated with demyelination in a nonhuman primate model of multiple sclerosis", J Immunol. Feb. 15, 1999;162(4):2384-90.

Ramos-Casals et al., "Autoimmune diseases induced by TNF-targeted therapies", Best Pract Res Clin Rheumatol. Oct. 2008;22(5):847-61.

Rossi et al., "CD20-targeted tetrameric interferon-alpha, a novel and potent immunocytokine for the therapy of B-cell lymphomas", Blood. Oct. 29, 2009;114(18):3864-71.

(56) References Cited

OTHER PUBLICATIONS

Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "Optimization of multivalent bispecific antibodies and immunocytokines with improved in vivo properties", Bioconjug Chem. Jan. 16, 2013;24(1):63-71.
Rossi et al., "A new class of bispecific antibodies to redirect T cells for cancer immunotherapy", MAbs. Mar.-Apr. 2014;6(2):381-91.
Sathish et al., "Challenges and approaches for the development of safer immunomodulatory biologics", Nat Rev Drug Discov. Apr. 2013;12(4):306-24.
Sharkey et al., "Improved cancer therapy and molecular imaging with multivalent, multispecific antibodies", Cancer Biother Radiopharm. Feb. 2010;25(1):1-12.
Singer, E., "Tysabri withdrawal calls entire class into question", Nat Med. Apr. 2005;11(4):359.
Van Noort et al., "Cell biology of autoimmune diseases", Int Rev Cytol. 1998;178:127-206.
Yang et al., "Human alpha 2-HS-glycoproteinibovine fetuin homologue in mice: identification and developmental regulation of the gene", Biochim Biophys Acta. Mar. 24, 1992;1130(2):149-56.
Yildirim-Toruner et a., "Current and novel therapeutics in the treatment of systemic lupus erythematosus", J Allergy Clin Immunol. Feb. 2011;127(2):303-12.
Abbas et al., Cellular and Molecular Immunology, W.B. Saunders Comp. 1991, p. 43.
Alto et al., "Bioinformatic design of A-kinase anchoring protein-in silica a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy" Cytokine Growth Factor Rev. 13(2)119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.

Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site", Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Vlyeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII", J. Biol. Chem. 271:29016-22 (1996).

(56) References Cited

OTHER PUBLICATIONS

Hodneland et al., "Selective immobilization of proteins to self-assembled monolayers presenting active site-directed capture ligands", Proc. Natl. Acd. Sci. USA 2002; 99:5048-5052.

Huang et al., "Targeting IFN-α to B Cell Lymphoma by a Tumor-Specific Antibody Elicits Potent Antitumor Activities" J. Immunol. 179:6881-88 (2007).

Hundsrucker et al., "High-affinity AKAP7σ-protein kinase A interaction yields novel protein kinase A-anchoring lisruptor peptides" Biochem. J. (2006) 396, 297-306.

Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).

Kinderman et al., "A Dynamic Mechanism for AKAP Binding to RII Isoforms of cAMP-Dependent Protein Kinase" Mol. Cell 24(3):397-408 (2006).

Kinstler et al., "Characterization and Stability of N-terminally PEGylated rhG-CSF" Pharm. Res. 1996;13 (7):996-1002.

Kramer et al., "Cell and virus sensitivity studies with recombinant human alpha interferons" J. Interferon. Res. 3 (4):425-35 (1983).

Le Bon et al., "Type I Interferons Potently Enhance Humoral Immunity and Can Promote Isotype Switching by Stimulating Dendritic Cells In Vivo" Immunity 14:461-470 (2001).

Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.

Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).

Luft et al., "Type I IFNs Enhance the Terminal Differentiation of Dendritic Cells" J. Immunol. 161:1947-1953 (1998).

Mason, Anthony J., "Functional Analysis of the Cysteine Residues of Activin A", Mol. Endocrinol. 8:325-32, 1994.

Matarrese et al., "Type I Interferon Gene Transfer Sensitizes Melanoma Cells to Apoptosis via a Target Activity on Mitochondrial Function" Am. J. Pathol. 2002, 160(4):1507-1520.

Henry, et al., "A prostate-specific membrane antigen-targeted monoclonal antibody-chemotherapeutic conjugate designed for the treatment of prostate cancer", Cancer Res. Nov. 1, 2004;64(21):7995-8001.

Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.

Newlon et al., "A Novel Mechanism of PKA Anchoring Revealed by Solution Structures of Anchoring Complexes", EMBO J. 2001; 20:1651-1662.

Newlon et al., "The molecular basis for protein kinase a anchoring revealed by solution NMR", Nature Struct. Biol. 1999; 3:222-227.

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).

Oyen et al., "Human testis cDNA for the regulatory subunit RIIα of cAMP-dependent protein kinase encodes an alternate amino-terminal region", FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-147 (1998).

Paquette et al., "Interferon-α and granulocyte-macrophage colony-stimulating factor differentiate peripheral blood monocytes into potent antigen-presenting cells" J. Leukoc. Biol. 64:358-367; 1998.

Pelham et al., "Interferon-α conjugation to human osteogenic sarcoma monoclonal antibody 791T/36" Cancer Immunol. Immuother. 1983;15(3):210-216.

Pepinsky et al., "Improved Pharmacokinetic Properties of a Poly-ethylene Glycol-Modified Form of Interferon-β-1a with Preserved in Vitro Bioactivity" Pharmacol. Exp. Ther. 2001; 297(3):1059-1066.

Pilling et al., "Interferon-β mediates stromal cell rescue of T cells from apoptosis" Eur. J. Immunol. 29:1041-1050 (1999).

Rabjohn et al., "Molecular Cloning and Epitope Analysis of the Peanut Allergen Ara h 3" J. Clinical Investigation 103 (4):535-542 (1999).

Raefsky et al., "Studies of Interferon as a regulator of hematopoietic cells proliferation" J. Immunol. 135 (4):2507-2512 (1985).

Rose et al., "Structural basis of dimerization, coactivator recognition and MODY3 mutations in HNF-1α", Nature Struct. Biol. 2000; 7:744-748.

Rosendahl et al., "A Long-Acting, Highly Potent Interferon α-2 Conjugate Created Using Site-Specific PEGylation" Bioconjugate Chem. 2005;16:200-207.

Rossi et al. "Novel Designs of Multivalent Anti-CD20 Humanized Antibodies as Improved Lymphoma Therapeutics", Cancer Res. 68:8384-92, 2008.

Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.

Rustandi et al., "The Ca2+-Dependent Interaction of s100B(ββ) with a Peptide Derived from p53", Biochemistry 1998; 37: 1951-1960.

Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.

Salles et al., "Rituximab combined with chemotherapy and interferon in follicular lymphoma patients: results of the GELA-GOELAMS FL2000 study" Blood 2008; 112:4824-4831.

Santini et al., "Type I Interferon as a Powerful Adjuvant for Monocyte-derived Dendritic Cell Development and Activity In Vivo and in Hu-PBL-SCID Mice" J. Exp. Med. 191(10)1777-1788 (2000).

Scott et al., "Type II Regulatory Subunit Dimerization Determines the Subcellular Localization of the cAMP-dependent Protein Kinase", J. Biol. Chem. 265:21561-66 (1990).

Scott et al., "Cyclic nucleotide-dependent protein kinases" Pharmacol. Ther. 1991;50(1)123-45.

Seffernick et al., "Melamine Deaminase and Atrazine Chlorohydrolase: 98 Percent Identical but Functionally Different" J. Bacteriol. 183(8):2405-2410 (2001).

Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al., "Metastatic Human Colonic Carcinoma: Molecular Imaging with Pretargeted SPECT and PET in a Mouse Model", Radiology 246:497-507, 2008.

Sidky et al., "Inhibition of Angiogenesis by Interferons: Effects on Tumor- and Lymphocyte-induced Vascular Responses" Cancer Res. 47:5155-5161, Oct. 1, 1987.

Stancovski et al., "Mechanistic aspects of the opposing effects of monoclonal antibodies to the ERBB2 receptor on humor growth", Proc Natl Acad Sci U S A. Oct. 1, 1991;88(19):8691-5.

Stein et al., "Characterization of a New Humanized Anti-CD20 Monoclonal Antibody, IMMU-106, and Its Use in combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab" Blood 2006;108:2736-2744.

(56) References Cited

OTHER PUBLICATIONS

Stokka et al., "Characterization of A-kinase-anchoring disruption using a solution-based assay" Biochem. J. (2006) 100, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence" Nature Jul. 31, 2003;424(6948):516-23.

Taylor, S., "cAMP-dependent Protein Kinase" J. Biol. Chem. 1989;264(15):8443-8446.

Walsh et al., "An Adenosine 3', 5'-Monophosphate-dependant Protein Kinase from Rabbit Skeletal Muscle" J. Biol. Chem. 243(13):3763-3774 (1968).

Weck et al., "Comparison of the Antiviral Activities of Various Cloned Human Interferon-α Subtypes in Mammalian Cell Cultures" J. Gen. Virol. (1981), 57, 233-237.

Winkler et al., "Changing the Antigen Binding Specificity by Single Point Mutations of an Anti-p24 (HIV-1) Antibody", J. Immunol. 165:4505-14, 2000.

Witkowski et al., "Conversion of a β-Ketoacyl Synthase to a Malonyl Decarboxylase by Replacement of the Active-Site Cysteine with Glutamine" Biochemistry 38(36):11643-50 (1999).

Wong et al., "AKAP Signalling Complexes: Focal Points in Space and Time", Nat. Rev. Mol. Cell Biol. 12:959-70 (2004).

Zhu et al., "Inhibition of tumor growth and metastasis by targeting tumor-associated angiogenesis with antagonists to the receptors of vascular endothelial growth factor", Invest. New Drugs 17:195-212, 1999.

\* cited by examiner

1. IFNα2b-DDD2 053006
2. IFNα2b-DDD2 010207
3. IFNα2b-DDD2 010207 30 mM Imidazole wash

PEGYLATION BY THE DOCK AND LOCK (DNL) TECHNIQUE

RELATED APPLICATIONS

The present application is a divisional of U.S. patent application Ser. No. 13/589,575 (now issued U.S. Pat. No. 9,457,100), filed Aug. 20, 2012, which was a divisional of U.S. patent application Ser. No. 13/150,613 (now issued U.S. Pat. No. 8,277,817), filed Jun. 1, 2011, which was a divisional of U.S. patent application Ser. No. 12/644,146 (now issued U.S. Pat. No. 7,981,398), filed Dec. 22, 2009, which was a divisional of U.S. patent application Ser. No. 11/925,408 (now issued U.S. Pat. No. 7,666,400), filed Oct. 26, 2007, which was a continuation-in-part of U.S. patent application Ser. No. 11/391,584 (now issued U.S. Pat. No. 7,521,056), filed Mar. 28, 2006, which claimed the benefit of U.S. Provisional Patent Applications 60/668,603 (now expired), filed Apr. 6, 2005; 60/751,196 (now expired), filed Dec. 16, 2005; and 60/782,332 (now expired), filed Mar. 14, 2006; and was a continuation-in-part of U.S. patent application Ser. No. 11/478,021 (now issued U.S. Pat. No. 7,534,866), filed Jun. 29, 2006, which claimed the benefit of U.S. Provisional Patent Applications 60/751,196 (now expired), filed Dec. 16, 2005; and 60/782,332 (now expired), filed Mar. 14, 2006; and was a continuation-in-part of U.S. patent application Ser. No. 11/633,729 (now issued U.S. Pat. No. 7,527,787), filed Dec. 5, 2006, which was a continuation-in-part of PCT/US06/10762, filed Mar. 24, 2006; PCT/US06/12084, filed Mar. 29, 2006; PCT/US06/25499, filed Jun. 29, 2006; U.S. patent application Ser. No. 11/389,358 (now issued U.S. Pat. No. 7,550,143), filed Mar. 24, 2006; Ser. No. 11/391,584 (now issued U.S. Pat. No. 7,521,056), filed Mar. 28, 2006; and Ser. No. 11/478,021 (now issued U.S. Pat. No. 7,534,866), filed Jun. 29, 2006; and claimed the benefit of U.S. Provisional Patent Applications 60/751,196 (now expired), filed Dec. 16, 2005; and 60/864,530 (now expired), filed Nov. 6, 2006; the text of each cited application incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on May 31, 2011, is named IBC18US9.txt and is 3,746 bytes in size.

BACKGROUND

The efficacy of a therapeutic agent may be enhanced by improving its bioavailability via several means, one of which is PEGylation, a process of chemically linking polyethylene glycol (PEG) to the therapeutic agent of interest, with the resulting conjugate exhibiting an increased serum half-life. Additional advantages of the PEGylated products may also include lower immunogenicity, decreased dosing frequency, increased solubility, enhanced stability, and reduced renal clearance. Because the most common reactive sites on proteins (including peptides) for attaching PEG are the $\epsilon$ amino groups of lysine and the $\alpha$ amino group of the N-terminal residue, early methods of PEGylation resulted in modification of multiple sites, yielding not only monoPEGylated conjugates consisting of mixtures of positional isomers, such as PEGINTRON™ (Grace et al., J. Biol. Chem. 2005; 280:6327) and PEGASYS® (Dhalluin et al., Bioconjugate Chem. 2005; 16:504), but also adducts comprising more than one PEG chain. Site-specific attachment of a single PEG to the α amino group of the N-terminal residue was reported to be the predominant product upon reacting PEG-aldehyde (PEG-ALD) at low pH with IFN-β1b (Basu et al., Bioconjugate Chem. 2006; 17:618) or IFN-β1a (Pepinsky et al., J. Pharmacol. Exp. Ther. 2001; 297:1059). Similar strategies were applied to prepare N-terminally linked PEG to G-CSF (Kinstler et al., Pharm. Res. 1996; 13:996) or type I soluble tumor necrosis factor receptor (Kerwin et al., Protein Sci. 2002; 11:1825). More recently, a solid-phase process for PEGylation of the N-terminus of recombinant interferon alpha-2a was reported (Lee et al., Bioconjug. Chem. Oct. 18, 2007, epub).

Site-directed PEGylation of a free cysteine residue introduced into a target protein has also been achieved with PEG-maleimide (PEG-MAL) for several recombinant constructs including IL-2 (Goodson and Katre, Biotechnology. 1990:8:343); IFN-α2 (Rosendahl et al., Bioconjugate Chem. 2005; 16:200); GM-CSF (Doherty et al., Bioconjugate Chem. 2005; 16:1291); scFv (Yang et al., Protein Eng. 2003; 16:761), and miniantibodies (Kubetzko et al., J. Biol. Chem; 2006; 201:35186). A popular approach for improving the therapeutic efficacy of an enzyme has been to prepare conjugates containing multiple PEG of small size, as known for methioninase (Yang et al., Cancer Res. 2004; 64:6673); L-methione γ-lyase (Takakura et al., Cancer Res. 2006:66: 2807): arginine deaminase (Wang et al., Bioconjugate Chem. 2006; 17:1447); adenosine deaminase (Davis et al., Clin. Exp. Immunol. 1981; 46:649); L-asparaginase (Bendich et al., Clin. Exp. Immunol. 1982; 48:273); and liver catalase (Abuchowski et al., J. Biol. Chem. 1977; 252:3582).

PEGylations of bovine serum albumin (Abuchowski et al., J. Biol. Chem. 1977; 252:3578); hemoglobin (Manjula et al., Bioconjugate Chem. 2003; 14:464); visomant (Mosharraf et al., Int. J. Pharm. 2007; 336:215); small molecules such as inhibitors of integrin α4β1 (Pepinsky et al., J. Pharmacol. Exp. Ther. 2005; 312:742); lymphoma-targeting peptides (DeNardo et al., Clin. Cancer. Res. 2003; 9(Suppl.): 3854s); anti-VEGF aptamer (Bunka and Stockley, Nat. Rev. Microbiol. 2006; 4:588) and oligodeoxynucleotides (Fisher et al., Drug Metab. Dispos. 2004; 32:983) have also been described. However, there exists a need for a general method of PEGylation that would produce exclusively a monoPEGylated conjugate composed of a single PEG linked site-specifically to a predetermined location of the candidate agent and retains the bioactivity of the unmodified counterpart.

SUMMARY OF THE INVENTION

The present invention discloses methods and compositions for producing PEGylated compounds with selected numbers of attached PEG residues that are attached at selected locations of a candidate agent. In preferred embodiments, the agents are monoPEGylated. In more preferred embodiments, the target to be PEGylated may be attached to a DDD (dimerization and docking domain) sequence and a PEG moiety may be attached to an AD (anchor domain) sequence as described in more detail below. Dimers of the DDD sequence bind with high affinity to monomers of the AD sequence, resulting in formation of a monoPEGylated target agent dimer. The stoichiometry of binding and location of the PEG residue are determined by the specificity of the DDD/AD interaction.

In more preferred embodiments, the monoPEGylated complex may be covalently stabilized by introduction of cysteine residues at appropriate locations in the DDD and AD sequences, to form disulfide bonds that stabilize the complex. In other embodiments, the PEG reagents may be capped at one end with a linear or branched methoxy group (m-PEG).

In other preferred embodiments, the PEGylated complex made by the DNL method shows a rate of clearance from serum that is at least an order of magnitude slower than the unPEGylated target agent. In certain alternative embodiments, the PEGylated complex may be alternatively constructed with the PEG moiety attached to the DDD sequence and the target agent attached to the AD sequence, resulting in a stoichiometry of 2 PEG to 1 target agent per complex.

The skilled artisan will realize that virtually any physiologically or therapeutically active agent to be administered in vivo may be stabilized by PEGylation, including but not limited to enzymes, cytokines, chemokines, growth factors, peptides, apatamers, hemoglobins, antibodies and fragments thereof. Exemplary agents include MIF, HMGB-1 (high mobility group box protein 1), TNF-$\alpha$, IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-23, IL-24, CCL19, CCL21, IL-8, MCP-1, RANTES, MIP-1A, MIP-1B, ENA-78, MCP-1, IP-10, Gro-$\beta$, Eotaxin, interferon-$\alpha$, -$\beta$, -$\lambda$, G-CSF, GM-CSF, SCF, PDGF, MSF, Flt-3 ligand, erythropoietin, thrombopoietin, hGH, CNTF, leptin, oncostatin M, VEGF, EGF, FGF, P1GF, insulin, hGH, calcitonin, Factor VIII, IGF, somatostatin, tissue plasminogen activator, and LIF.

The monoPEGylated complexes, are suitable for use in a wide variety of therapeutic and diagnostic applications. Methods of use of monoPEGylated complexes may include detection, diagnosis and/or treatment of a disease or other medical condition. Such conditions may include, but are not limited to, cancer, hyperplasia, diabetes, diabetic retinopathy, macular degeneration, inflammatory bowel disease, Crohn's disease, ulcerative colitis, rheumatoid arthritis, sarcoidosis, asthma, edema, pulmonary hypertension, psoriasis, corneal graft rejection, neovascular glaucoma, Osler-Webber Syndrome, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis or wound granulation.

In particular embodiments, the disclosed methods and compositions may be of use to treat autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, juvenile diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

It is anticipated that any type of tumor and any type of tumor antigen may be targeted. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

DOCK AND LOCK (DNL) METHOD

The key to the DNL method is the exploitation of the specific protein/protein interactions occurring in nature between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathway triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and MI), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561).

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

Figure 1:
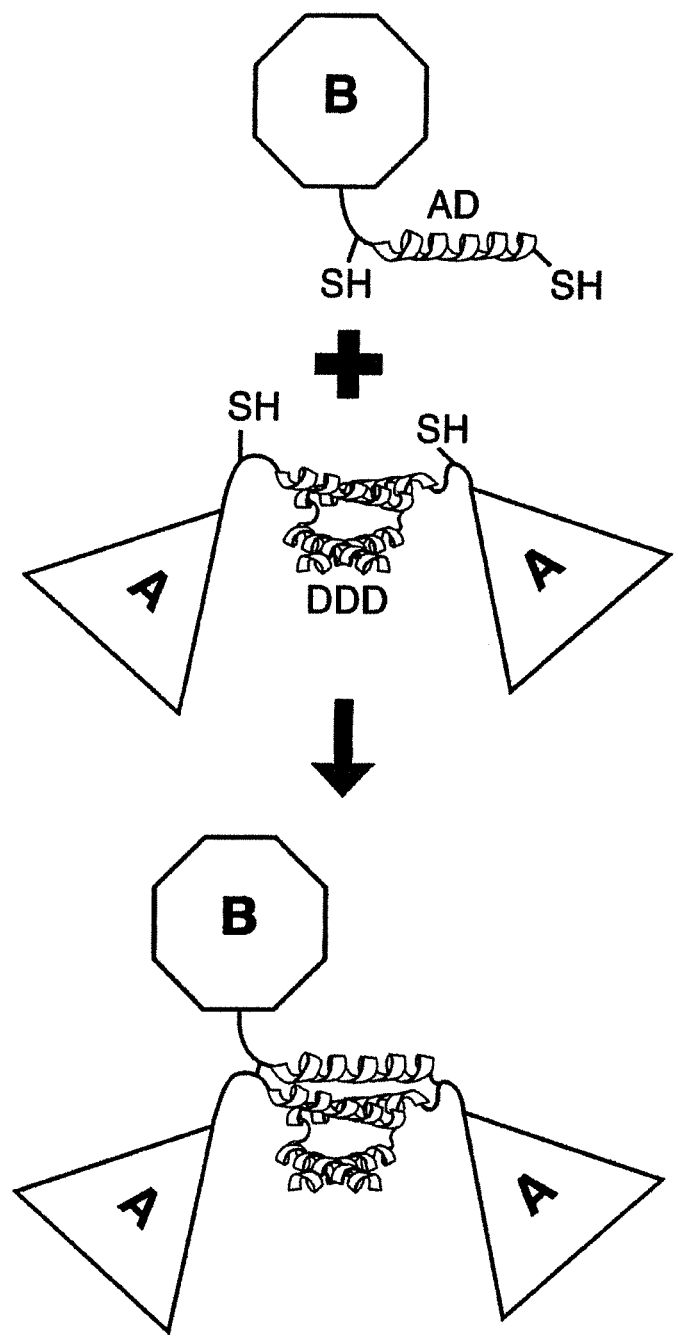
FIG. 1. Cartoon illustration of the DNL method. Triangles depict component A, which forms a homodimer ($a_2$) mediated by the dimerization and docking domain (DDD). The location of free thiol groups (SH) of the engineered cysteine residues is indicated. Octagons depict component B containing an anchor domain (AD) peptide. The DNL reaction results in the generation of a covalent trimeric structure via binding of DDD and AD peptides and subsequent formation of disulfide bridges.

We have developed a platform technology to utilize the DDD of human RIIα and the AD of a certain amino acid sequence as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds, as illustrated in FIG. 1. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2$b. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, nucleic acids, and PEG. The DNL method was disclosed in each of the following U.S. Provisional patent applications: 60/728,292, filed Oct. 20, 2005; 60/751,196, filed Dec. 16, 2005; and 60/782,332, filed Mar. 14, 2006, and U.S. patent application Ser. No. 11/389,358, all incorporated herein by reference in their entirety.

PEGylation by DNL

In a preferred method, the target to be PEGylated is linked to a DDD sequence to generate the DDD module. A PEG reagent of a desirable molecular size is derivatized with a related AD sequence and the resulting PEG-AD module is combined with the DDD module to produce the PEGylated conjugate that consists of a single PEG tethered site-specifically to two copies of the target via the disulfide bonds formed between DDD and AD. The PEG reagents are capped at one end with a methoxy group (m-PEG), can be linear or branched, and may contain one of the following functional groups: propionic aldehyde, butyric aldehyde, ortho-pyridylthioester (OPTE), N-hydroxysuccinimide (NETS), thiazolidine-2-thione, succinimidyl carbonate (SC), maleimide, or ortho-pyridyldisulfide (OPPS). Among the targets that may be of interest for PEGylation are enzymes, cytokines, chemokines, growth factors, peptides, aptamers, hemoglobins, antibodies and fragments. The method is not limiting and a wide variety of agents may be PEGylated using the disclosed methods and compositions.

EXAMPLES

The following examples are provided to illustrate, but not to limit, the claims of the present invention.

Example 1

Generation of PEG-AD2 Modules

Synthesis of IMP350

(SEQ ID NO: 1)
CGQIEYLAKQIVDNAIQQAGC(SS-tbu)-NH$_2$ MH$^+$2354

IMP350 was made on a 0.1 mmol scale with Sieber Amide resin using Fmoc methodology on a Protein Technologies PS3 peptide synthesizer. Starting from the C-terminus the protected amino acids used were Fmoc-Cys(t-Buthio)-OH, Fmoc-Gly-OH, Fmoc-Ala-OH, Fmoc-Gln (Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH and Fmoc-Cys(Trt)-OH. The peptide was cleaved from the resin and purified by reverse phase (RP)-HPLC.

Synthesis of PEG$_{20}$-IMP350

IMP350 (0.0104 g) was mixed with 0.1022 g of mPEG-OPTE (20 kDa, Nektar Therapeutics) in 7 mL of 1 M Tris buffer at pH 7.81. Acetonitrile, 1 mL, was then added to dissolve some suspended material. The reaction was stirred at room temperature for 3 h and then 0.0527 g of TCEP was added along with 0.0549 g of cysteine. The reaction mixture was stirred for 1.5 h and then purified on a PD-10 desalting column, which was equilibrated with 20% methanol in water. The sample was eluted, frozen and lyophilized to obtain 0.0924 g of crude PEG$_{20}$-IMP350 (MH+23508 by MALDI).

Synthesis of IMP360

(SEQ ID NO: 9)
CGQIEYLAKQIVDNAIQQAGC(SS-tbu)G-EDANS MH$^+$ 2660

IMP 360 was synthesized on a 0.1 mmol scale with EDANS resin (Nova Biochem) using Fmoc methodology on a Protein Technologies PS3 peptide synthesizer. The Fmoc-Gly-OH was added to the resin manually using 0.23 g of Fmoc-Gly-OH, 0.29 g of HATU, 26 µL of DIEA, 7.5 mL of DMF and 0.57 g of EDANS resin (Nova Biochem). The reagents were mixed and added to the resin. The reaction was mixed at room temperature for 2.5 hr and the resin was washed with DMF and IPA to remove the excess reagents. Starting from the C-terminus the protected amino acids used were Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH and Fmoc-Cys(Trt)-OH. The peptide was cleaved from the resin and purified by RP-HPLC.

Synthesis of IMP362 (PEG$_{20}$-IMP360)

Figure 2:
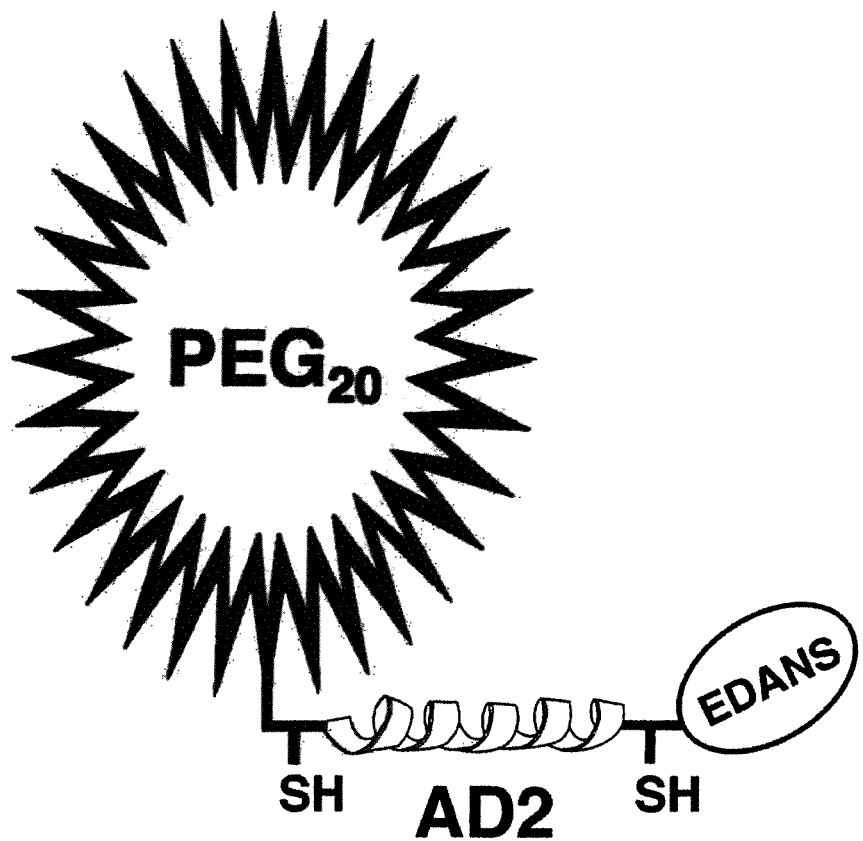
FIG. 2. Cartoon drawing of IMP362. A 20 kDa PEG (starburst), AD2 peptide (helix), EDANS fluorescent tag (oval) and the positions of free sulfhydryl groups (SH) are indicated.

A cartoon diagram of IMP362 is provided in FIG. 2. For synthesis of IMP362, IMP360 (0.0115 g) was mixed with 0.1272 g of mPEG-OPTE (20 kDa, Nektar Therapeutics) in 7 mL of 1 M tris buffer, pH 7.81. Acetonitrile (1 mL) was then added to dissolve some suspended material. The reaction was stirred at room temperature for 4 h and then 0.0410 g of TCEP was added along with 0.0431 g of cysteine. The reaction mixture was stirred for 1 h and purified on a PD-10 desalting column, which was equilibrated with 20% methanol in water. The sample was eluted, frozen and lyophilized to obtain 0.1471 g of crude IMP362 (MH+23713).

Synthesis of IMP413 (PEG$_{30}$-IMP360)

Figure 3:
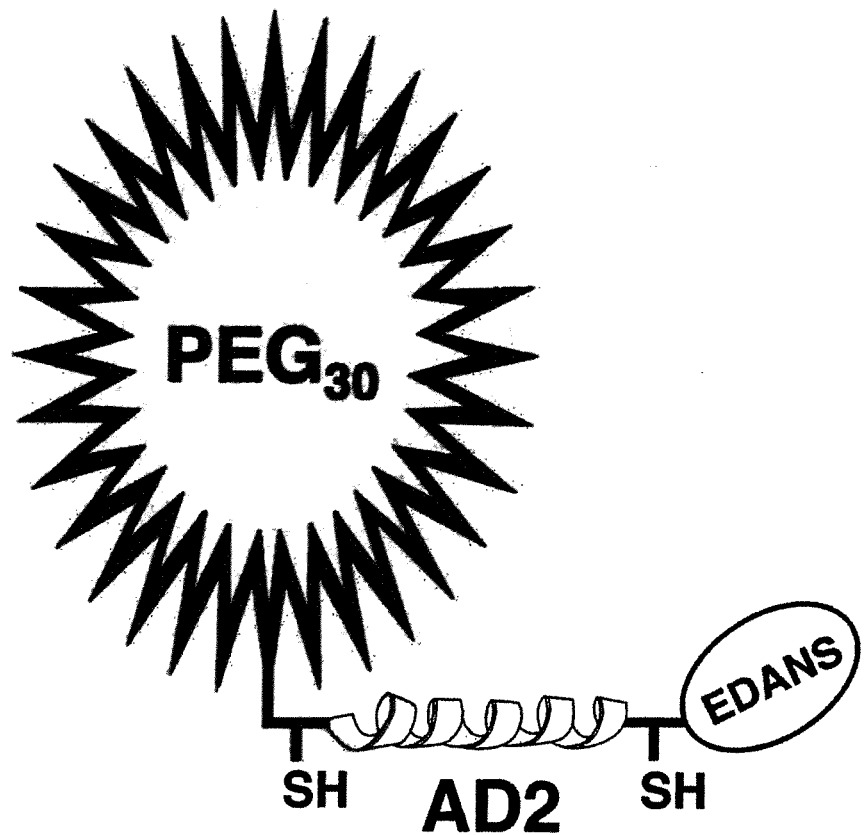
FIG. 3. Cartoon drawing of IMP413. A 30 kDa PEG (starburst), AD2 peptide (helix), EDANS fluorescent tag (oval) and the positions of free sulfhydryl groups (SH) are indicated.

A cartoon diagram of IMP 413 is provided in FIG. 3. For synthesis of IMP 413, IMP 360 (0.0103 g) was mixed with 0.1601 g of mPEG-OPTE (30 kDa, Nektar Therapeutics) in 7 mL of 1 M tris buffer at pH 7.81. Acetonitrile (1 mL) was then added to dissolve some suspended material. The reaction was stirred at room temperature for 4.5 h and then 0.0423 g of TCEP was added along with 0.0473 g of cysteine. The reaction mixture was stirred for 2 h followed by dialysis for two days. The dialyzed material was frozen and lyophilized to obtain 0.1552 g of crude IMP413 (MH+ 34499).

Example 2

Generation of DDD Module Based on Interferon (IFN)-α2b

Construction of IFN-α2b-DDD2-pdHL2 for Expression in Mammalian Cells

The cDNA sequence for IFN-α2b was amplified by PCR, resulting in a sequence comprising the following features, in which XbaI and BamHI are restriction sites, the signal peptide is native to IFN-α2b, and 6 His is a hexahistidine tag (SEQ ID NO: 10): XbaI---Signal peptide---IFNα2b---6 His---BamHI ("6 His" disclosed as SEQ ID NO: 10). The resulting secreted protein will consist of IFN-α2b fused at its C-terminus to a polypeptide consisting of SEQ ID NO:2.

(SEQ ID NO: 2)
KSHHHHHHGSGGGGSGGGCGHIQIPPGLTELLQGYTVEVLRQQPPDLVEF

AVEYFTRLREARA

PCR amplification was accomplished using a full length human IFNα2b cDNA clone (Invitrogen Ultimate ORF human clone cat# HORFO1Clone ID IOH35221) as a template and the following oligonucleotides as primers:

IFNA2 Xba I Left
(SEQ ID NO: 3)
5'-TCTAGACACAGGACCTCATCATGGCCTTGACCTTTGCTTTACTG

G-3'

IFNA2 BamHI right
(SEQ ID NO: 4)
5'-GGATCCATGATGGTGATGATGGTGTGACTTTTCCTTACTTCTTAAA

CTTTCTTGC-3'

The PCR amplimer was cloned into the pGemT vector (Promega). A DDD2-pdHL2 mammalian expression vector was prepared for ligation with IFN-α2b by digestion with XbaI and Bam HI restriction endonucleases. The IFN-α2b amplimer was excised from pGemT with XbaI and Bam HI and ligated into the DDD2-pdHL2 vector to generate the expression vector IFN-α2b-DDD2-pdHL2.

Mammalian Expression of IFN-α2b-DDD2

IFN-α2b-DDD2-pdHL2 was linearized by digestion with SalI enzyme and stably transfected into Sp/EEE myeloma cells by electroporation (see. e.g., U.S. patent application Ser. No. 11/487,215, filed Jul. 14, 2006, incorporated herein by reference). Two clones were found to have detectable levels of IFN-α2b by ELISA. One of the two clones, designated 95, was adapted to growth in serum-free media without substantial decrease in productivity. The clone was subsequently amplified with increasing methotrexate (MTX) concentrations from 0.1 to 0.8 μM over five weeks. At this stage, it was sub-cloned by limiting dilution and the highest producing sub-clone (95-5) was expanded. The productivity of 95-5 grown in shake-flasks was estimated to be 2.5 mg/L using commercial rIFN-α2b (Chemicon IF007, Lot 06008039084) as a standard.

Purification of IFN-α2b-DDD2 from Batch Cultures Grown in Roller Bottles

Figure 4:
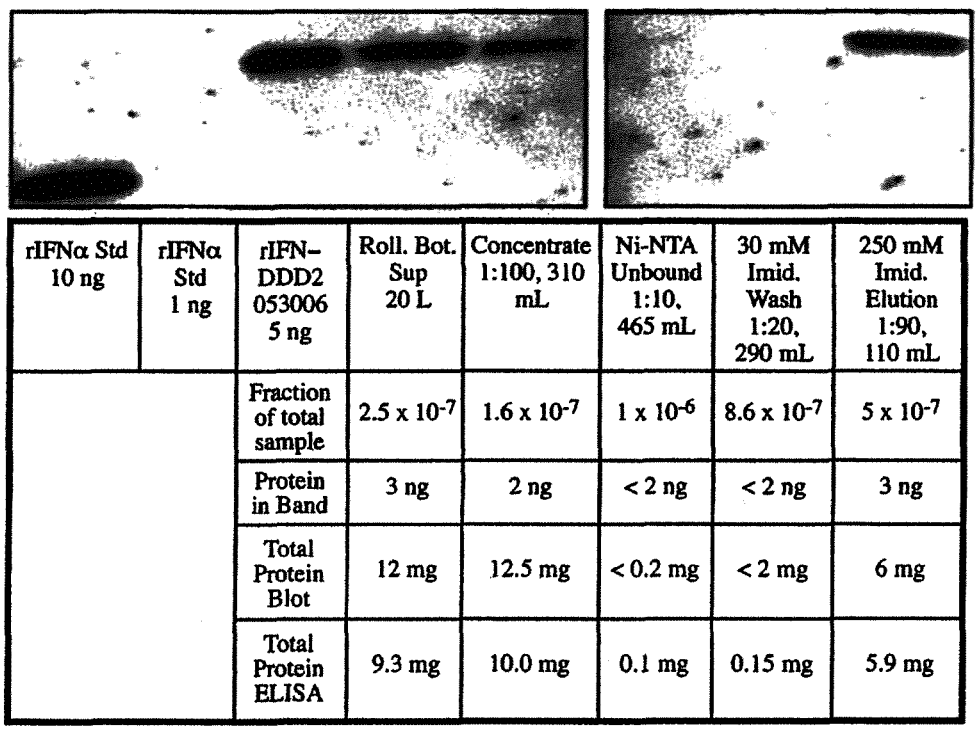
FIG. 4. Analysis of roller bottle production and purification by anti-IFNa immunoblot and ELISA. Samples were diluted as indicated and 5 µl were subjected to reducing SDS-PAGE and immunoblot analysis with polyclonal anti-IFNa. The dilution, total volume and fraction analyzed of the total volume (f) for each sample is given. The amount of protein in each band was estimated from standards and divided by f to give the total protein estimate. Total protein measurements determined by ELISA are also given.

Clone 95-5 was expanded to 34 roller bottles containing a total of 20 L of serum-free Hybridoma SFM with 0.8 μM MTX and allowed to reach terminal culture. The supernatant fluid was clarified by centrifugation, filtered (0.2 μM). The filtrate was diafiltered into 1× Binding buffer (10 mM imidazole, 0.5 M NaCl, 50 mM $NaH_2PO_4$, pH 7.5) and concentrated to 310 mL in preparation for purification by immobilized metal affinity chromatography (IMAC). The concentrate was loaded onto a 30-mL Ni-NTA column, which was washed with 500 mL of 0.02% Tween 20 in 1× binding buffer and then 290 mL of 30 mM imidazole, 0.02% Tween 20, 0.5 M NaCl, 50 mM $NaH_2PO_4$, pH 7.5. The product was eluted with 110 mL of 250 mM imidazole, 0.02% Tween 20, 150 mM NaCl, 50 mM $NaH_2PO_4$, pH 7.5. Approximately 6 mg of IFNα2b-DDD2 was purified. FIG. 4 shows the results of an anti-IFNa immunoblot and ELISA used to quantify IFNα2b-DDD2.

Characterization of IFN-α2b-DDD2

Figure 5:
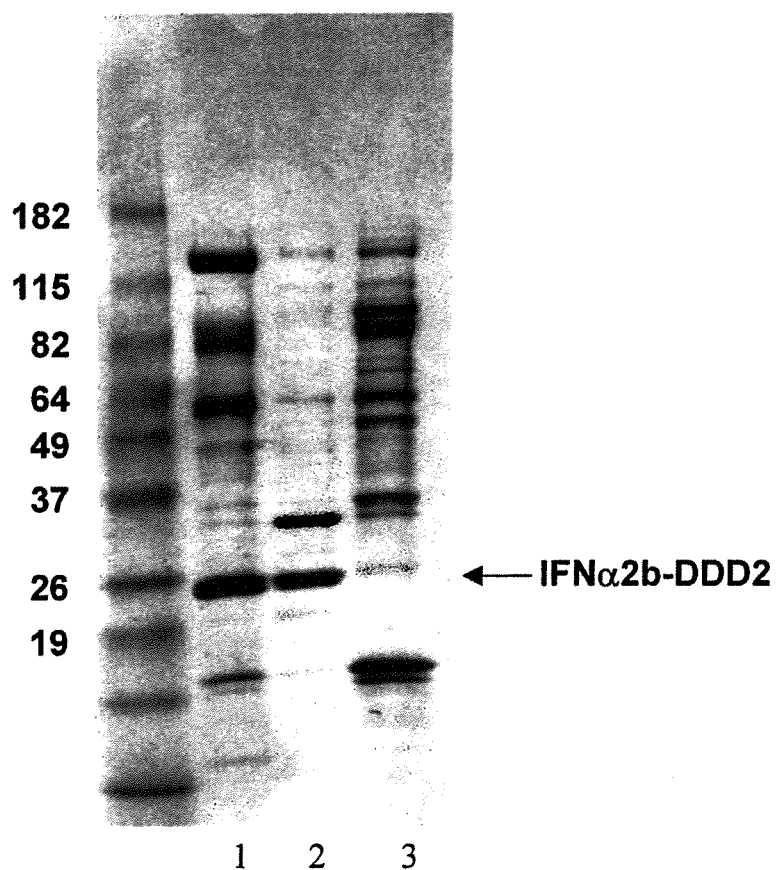
FIG. 5. Reducing SDS-PAGE analysis of IFN$\alpha$2b-DDD2 following IMAC purification with Ni-NTA. Two independent preparations of IFN$\alpha$2b-DDD2 (lanes 1 & 2), which were eluted from Ni-NTA resin with 250 mM imidazole buffer, and the 30 mM imidazole buffer column wash were resolved by SDS-PAGE under reducing conditions and stained with Coomassie blue. The position of $M_r$ standards and IFN$\alpha$2b-DDD2 (arrow) are indicated.

The purity of IFN-α2b-DDD2 was assessed by SDS-PAGE under reducing conditions (FIG. 5). The Coomassie blue-stained gel shows that the batch produced from roller bottles (lane 2) was purer than an earlier batch (lane 1). IFN-α2b-DDD2 was the most heavily stained band and accounts for approximately 50% of the total protein. The product resolves as a doublet with an $M_r$ of ~26 kDa, which is consistent with the calculated MW of IFN-α2b-DDD2-SP (26 kDa). There is one major contaminant with a $M_r$ of 34 kDa and many faint contaminating bands.

Example 3

Generation of PEGylated IFN-α2b by DNL

Preparation and Purification of α2b-362 (IFN-α2b-DDD2-IMP 362)

Figure 6:
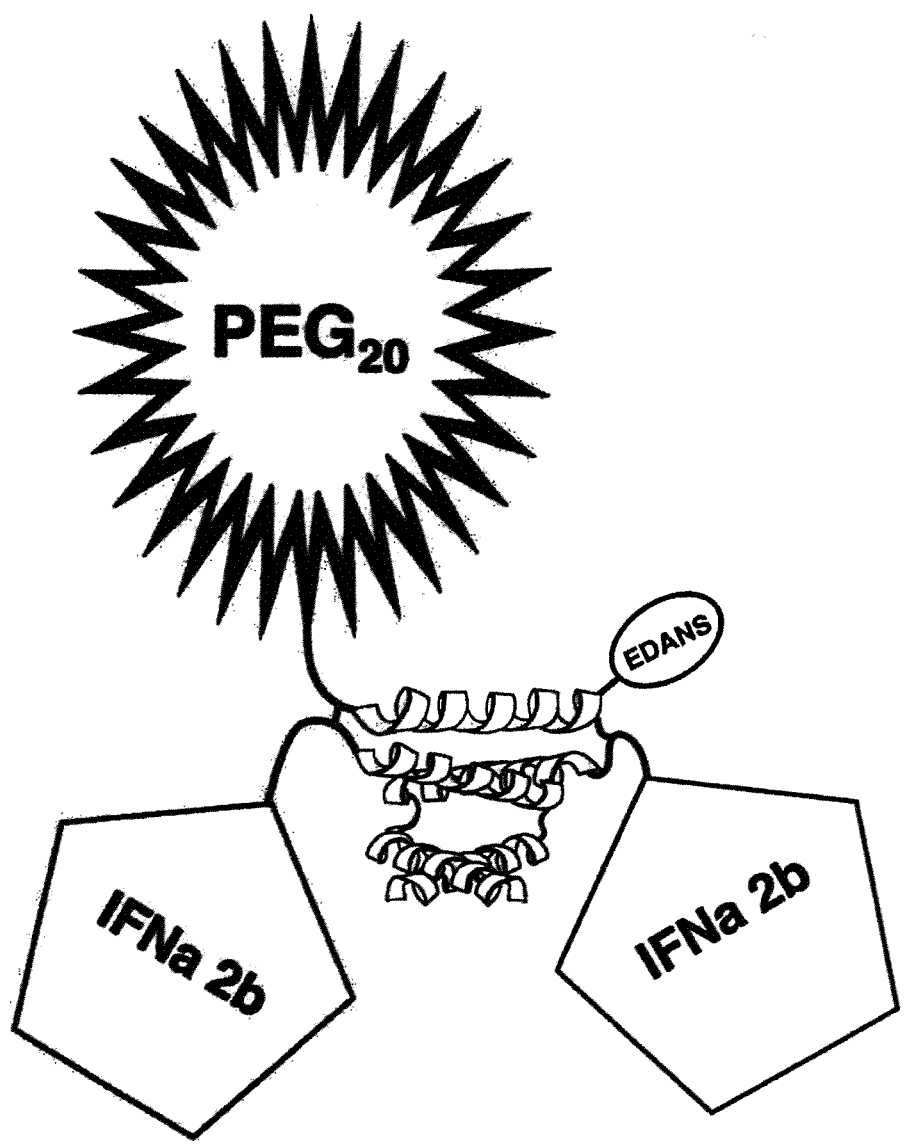
FIG. 6. Cartoon drawing of $\alpha$2b-362. IFN$\alpha$2b groups (pentagons), 20 kDa PEG (starburst), AD2 and DDD2 peptides (helices) and EDANS fluorescent tag (oval) are indicted.

A cartoon drawing depicting the structure of α2b-362 having two copies of IFNα2b coupled to a 20 kDa PEG is provided in FIG. 6. A DNL reaction was performed by the addition of 11 mg of reduced and lyophilized IMP362 in 10-fold molar excess to 2.25 mg (3.5 ml) of IFN-α2b-DDD2 in 250 mM imidazole, 0.02% Tween 20, 150 mM NaCl, 1 mM EDTA, 50 mM $NaH_2PO_4$, pH 7.5. After 6 h at room temperature in the dark, the reaction mixture was dialyzed against CM Loading Buffer (150 mM NaCl, 20 mM NaAc, pH 4.5) at 4° C. in the dark. The solution was loaded onto a 1-mL Hi-Trap CM-FF column (Amersham), which was pre-equilibrated with CM Loading buffer. After sample loading, the column was washed with CM loading buffer to baseline, followed by washing with 15 mL of 0.25 M NaCl, 20 mM NaAc, pH 4.5. The PEGylated product was eluted with 12.5 mL of 0.5 M NaCl, 20 mM NaAc, pH 4.5.

Figure 7:
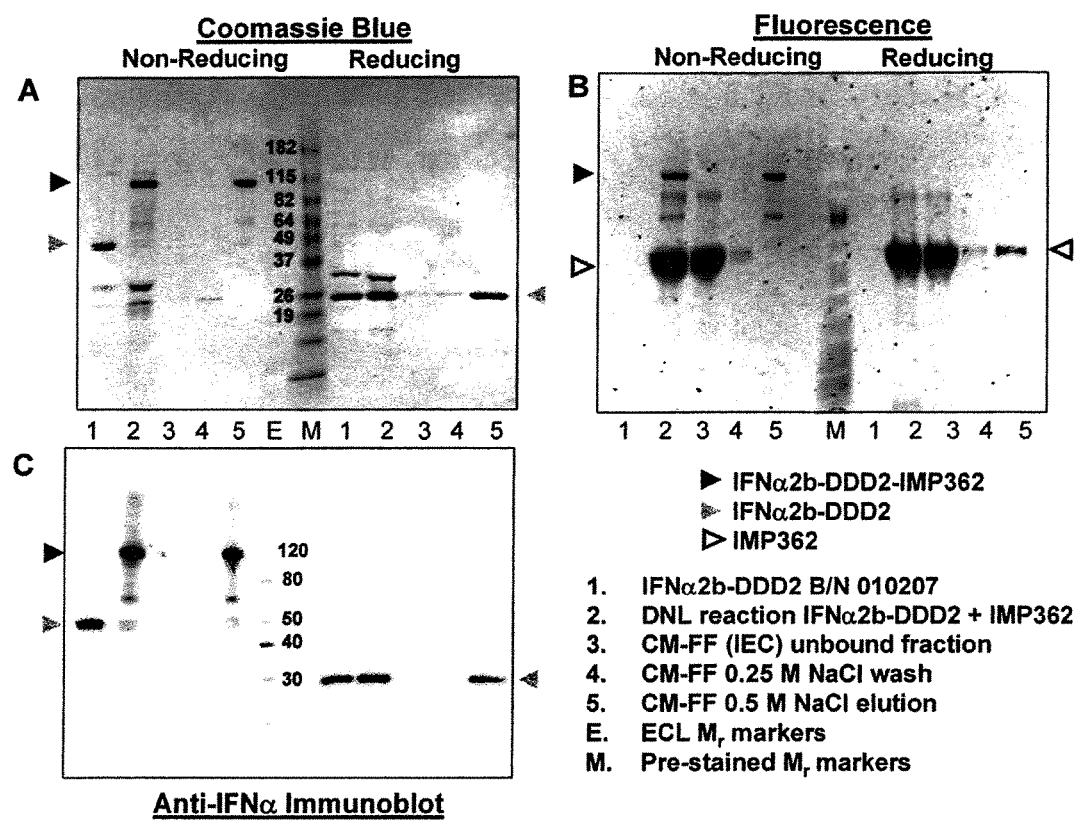
FIG. 7. Analysis of CM-FF IEC purification of IFN$\alpha$2b-DDD2-IMP362 by SDS-PAGE with Coomassie Blue staining (A), direct fluorescence imaging (B) and anti-IFN$\alpha$ immunoblotting (C). The same gel was used for fluorescence imaging and subsequent Coomassie blue staining. For this gel (A+B), all fractions were concentrated to correspond to the reaction volume (3.5 mL) and 5 µl/lane were loaded. Both reduced and non-reduced samples were run as indicated. For the immunoblot (C), all samples were diluted 1:50 from those used for gel A/B. Solid black, grey and open arrow-heads show the positions of IFN$\alpha$2b-DDD2-IMP362, IFN$\alpha$2b-DDD2 and IMP362, respectively. The positions of $M_r$ standards are also indicated.

The conjugation process was analyzed by SDS-PAGE with Coomassie blue staining (FIG. 7A), fluorescence imaging (FIG. 7B) and anti-IFNα immunoblotting (FIG. 7C). To normalize the samples for direct protein mass comparison, each fraction eluted from the CM-FF column was concentrated to 3.5 mL to match the reaction volume. Under non-reducing conditions, the Coomassie blue-stained gel (FIG. 7A) revealed the presence of a major band at a $M_r$ of 110 kDa (lane 2) in the reaction mixture, which was absent in the unbound (lane 3) or 0.25 M NaCl wash fraction (lane 4), but evident in the 0.5 M NaCl fraction (lane 5). Fluorescence imaging (FIG. 7B), which was used to detect the EDANS tag on IMP362, demonstrates that the 110 kDa band contains IMP362 (lanes 2 and 5) and the presence of excess IMP362 in the reaction mixture (lane 2) and the unbound fraction (lane 3), which does not stain with Coomassie blue. Anti-IFNα immunoblotting (FIG. 7C) confirms the association of IFN-α2b with the 110 kDa band (lanes 2 and 5). These data together indicate that the DNL reaction results in the site-specific and covalent conjugation of IMP362 with a dimer of IFN-α2b. Under reducing conditions, which breaks the disulfide linkage, the components of the DNL structures are resolved. The calculated MW of α2b-362 is ~75 kDa, which matches well the mass of 76,728 Da determined by MALDI TOF. The observed discrepancy between the calculated mass and the estimated Mr by SDS-PAGE is due to PEG, which is known to inflate the molecular size when PEGylated products are analyzed by SDS-PAGE or SE-HPLC. Overall, the DNL reaction resulted in a near quantitative yield of a homogeneous product that is >90% pure after purification by cation-exchange chromatography.

Preparation and Purification of α2b-413 (IFN-α2b-DDD2-IMP413)

Figure 8:
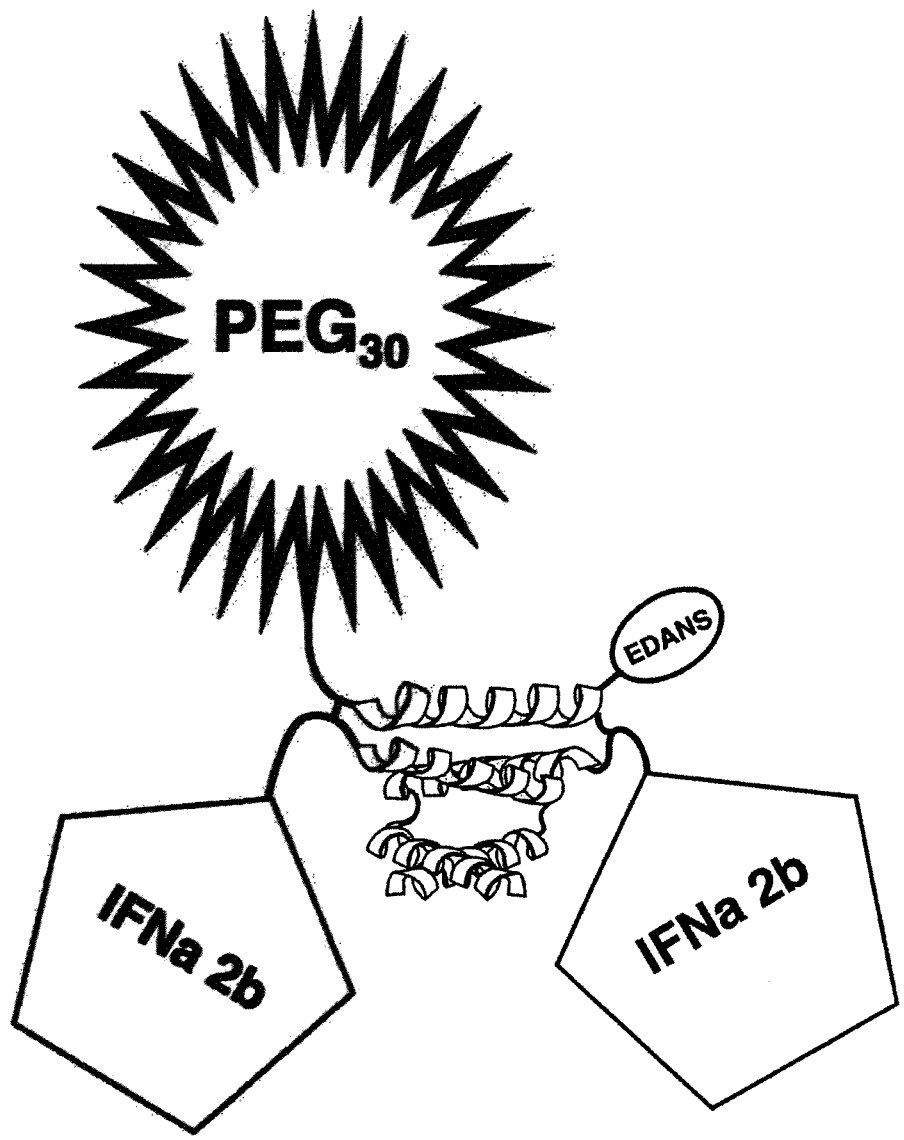
FIG. 8. Cartoon drawing of $\alpha$2b-413. IFN$\alpha$2b groups (pentagons), 30 kDa PEG (starburst), AD2 and DDD2 peptides (helices) and EDANS fluorescent tag (oval) are indicted.

A cartoon drawing depicting the structure of α2b-413 having two copies of IFNα2b coupled to a 30 kDa PEG is provided in FIG. 8. α2b-413 was prepared as described immediately above using IMP413 instead of IMP362.

Example 4

Evaluation of the in vitro potency of IFN-α2b-DDD2, α2b-362, and α2b-413

In Vitro Anti Proliferative Assay

Figure 9:
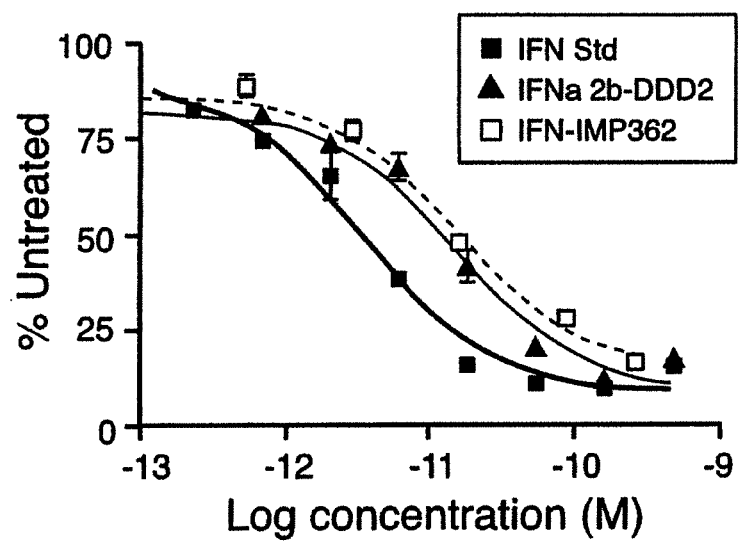
FIG. 9. Dose-response curves showing in vitro growth inhibition of Burkitt's lymphoma (Daudi) cells after 4-days in culture in the presence of either rhIFN-α2b standard, IFN-α2b-DDD2 or α2b-362. MTS dye was added to the plates, which were incubated for 3 h before measuring the $OD_{490}$. The % of the signal obtained from untreated cells was plotted vs. the log of the molar concentration. The 50% effective concentration ($EC_{50}$) values were obtained by sigmoidal fit non-linear regression using Graph Pad Prism software.

IFN-α2b-DDD2 and α2b-362 were assayed for inhibition of growth of Burkitt's lymphoma (Daudi) cells. Briefly, IFN-α2b standard (Chemicon IF007, Lot 06008039084), IFN-α2b-DDD2 (batch 010207) and α2b-362 (batch 010807) were each diluted to 500 pM in RPMI 1640 media supplemented with 10% FBS, from which three-fold serial dilutions in triplicate were made in 96-well tissue culture plates (50 μL sample/well). Daudi cells were diluted to $4 \times 10^5$ cells/mL and 50 μL were added to each well (20K/well). The concentration range for each test reagent was 500 pM to 0.008 pM. After 4 days at 37° C., MTS dye was added to the plates (20 μL per well) and after 3 h the plates were read with an Envision plate reader (Perkin Elmer, Boston Mass.) at 490 nm. Dose-response curves were generated (FIG. 9) and 50% effective concentration ($EC_{50}$) values were obtained by sigmoidal fit non-linear regression using Graph Pad Prism software (Advanced Graphics Software, Encinitas, Calif.). The calculated $EC_{50}$ for IFNα2b-DDD2 and α2b-362 were similar (~16 pM) and about 5-fold less potent than the IFN-α2b standard ($EC_{50}$~4 pM). In a similar experiment the α2b-413 had similar potency as α2b-362.

Anti-Viral Assay

Duplicate samples were analyzed in a viral challenge assay using encephalomyocarditis (EMC) virus on A549 cells by an independent analytical laboratory (PBL Interferon Source, Piscataway, N.J.). Plates were stained with crystal violet and the OD was measured by spectrophotometry on a 96-well plate reader following solubilization of the dye. The data were analyzed with Graph Pad Prizm software using a sigmoidal fit (variable slope) non-linear regression. The anti-viral titer was determined by comparison of $EC_{50}$ values with that of an IFNa standard. The specific anti-viral activities were calculated at $1.2 \times 10^8$ U/mg and $8.8 \times 10^6$ U/mg for α2b-362 and α2b-413, respectively.

Example 5

In Vivo Evaluation of α2b-413 and α2b-362

Pharmacokinetics

The study was performed in adult female Swiss-Webster mice (~35 g). There were 4 different treatment groups of 2 mice each. Each reagent (test and control) was administered at equimolar protein doses (3 μg of rhuIFN-α2a, 5 μg of PEGINTRON™, 11 μg of α2b-362, and 13 μg of α2b-413) as a single bolus i.v. injection. Mice were bled via the retro-orbital method at various time-points (pre-dose, 5-min, 2-, 8-, 24-, 48-, 72-, 96-, and 168-h post-injection). The blood was allowed to clot, centrifuged, and the serum was isolated and stored at −70° C. until assayed for IFN-α concentration and subsequent PK-analysis.

Figure 10:
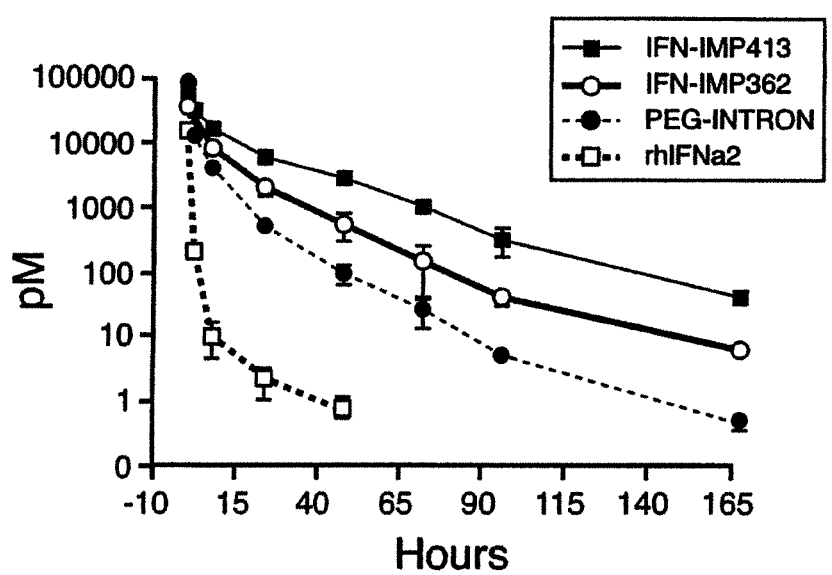
FIG. 10. Evaluation of the pharmacokinetic properties of IFNα constructs. Each reagent (test and control) was administered to Swiss-Webster mice at equimolar protein doses as a single bolus i.v. injection of 3 μg for rhuIFN-α2a, 5 μg for PEGINTRON™, 11 μg for α2b-362, and 13 μg for α2b-413. Serum samples were isolated at the times indicated and the serum concentrations of IFN-α were determined by ELISA. The pM concentration was plotted vs. hours post injection. Data represents the mean value from two mice.

Concentrations of IFN-α in the serum samples were determined using a human interferon alpha ELISA kit following the manufacturers instructions (PBL Interferon Source). Briefly, the serum samples were diluted appropriately according to the human IFN-α standard provided in the kit. An antibody coupled to the microtiter plate wells captures interferon. A second antibody is then used to reveal the bound interferon, which is quantified by anti-secondary antibody conjugated to horseradish peroxidase (HRP) following the addition of Tetramethyl benzidine (TMB) substrate. The plates were read at 450 nm, and the results are shown in FIG. 10.

The PK properties of each agent are summarized in Table 1. As expected, rhIFN-α2a had the most rapid clearance from the blood of injected mice. Its clearance was approximately 3-fold faster than the PEGINTRON™ and more than 13-fold faster than the DNL-IFN reagents. The PEGINTRON™ was in turn cleared greater than 4-fold faster than α2b-362 or α2b-413. There was little difference in the elimination rates between α2b-362 and α2b-413.

TABLE 1

Blood Pharmacokinetic Analysis of Interferon-α2b Containing DNL Molecules Administered as Intravenous Injections to Naive Swiss-Webster Mice.

| Animal Number | IFN Dose (pmol) | $C_{max}$ (pM) | $T_{1/2\alpha}$ (hours) | $T_{1/2\beta}$ (hours) | $AUC_{0.08 \to \infty}$ (h * pM) | Elimination Rate (1/h) | $MRT_{0.08 \to \infty}$ (h) |
|---|---|---|---|---|---|---|---|
| Recombinant Human Interferon-α2a ||||||||
| Animal No. 1 | 160 | 16,411 | 0.29 | 10.53 | 7,011 | 2.34 | 0.63 |
| Animal No. 2 | 160 | 21,835 | 0.31 | 7.14 | 10,147 | 2.15 | 0.78 |
| Mean | 160 | 19,123 | 0.30 | 8.84 | 8,579 | 2.25 | 0.71 |
| PEG-INTRON ||||||||
| Animal No. 1 | 160 | 87,090 | 0.53 | 6.29 | 137,790 | 0.63 | 5.42 |
| Animal No. 2 | 160 | 105,774 | 0.43 | 5.11 | 150,905 | 0.70 | 4.79 |
| Mean | 160 | 96,432 | 0.48 | 5.70 | 144,348 | 0.67 | 5.11 |

TABLE 1-continued

IFN-α2b-IMP362

| | | | | | | |
|---|---|---|---|---|---|---|
| Animal No. 1 | 320 | 60,833 | 1.72 | 7.54 | 379,462 | 0.16 | 9.03 |
| Animal No. 2 | 320 | 97,089 | 1.43 | 10.14 | 570,336 | 0.17 | 11.56 |
| Mean | 320 | 78,961 | 1.58 | 8.84 | 474,899 | 0.17 | 10.30 |

IFN-α2b-IMP413

| | | | | | | |
|---|---|---|---|---|---|---|
| Animal No. 1 | 320 | 152,923 | 0.69 | 12.85 | 1,012,470 | 0.15 | 16.75 |
| Animal No. 2 | 320 | 100,495 | 4.03 | 28.53 | 1,179,056 | 0.09 | 26.56 |
| Mean | 320 | 126,709 | 2.36 | 20.69 | 1,095,763 | 0.12 | 21.66 |

In terms of mean residence time (MRT), there is a clear correlation with size among the various reagents. The 19-kDa rhIFN-α2a had a MRT that was 7-fold less than the 31 kDa PEGINTRON™ (0.7 h versus 5.1 h, respectively), which had a 2-fold lower MRT when compared to the 70 kDa α2b-362 (10.3 h). The MRT for the 80 kDa α2b-413 (21.7 h) was 2-fold longer than α2b-362. Finally, a test for bioequivalence showed that none of the reagents tested were the same in terms of PK, indicating that the differences are genuine (i.e., circulating half-life for α2b-413>α2b-362>PEGINTRON™>rhIFN-α2a).

Anti-Tumor Therapeutic Efficacy

An initial in vivo tumor therapy study demonstrated that the DNL-PEGylated interferons were more potent and longer-lasting compared to PEGINTRON™. Eight-week-old female C.B.-17 SCID mice were injected i.v. with a human Burkitt's lymphoma cell-line (Daudi) at $1.5 \times 10^7$ cells per animal. There were 10 different treatment groups of 5 mice each. Equivalent units of activity of PEGINTRON™, α2b-362 and α2b-413 were administered once every 7 days via s.c. injection in either the left or right flank at three different doses (3500, 7000, and 14000 Units). Therapy commenced 1 day after the Daudi cells were transplanted.

Mice were observed daily for signs of distress and paralysis. They were weighed weekly. In the event a mouse or mice lost greater than 15% of its body weight (but <20%) it was weighed every 2 days until it either gained back its weight to <15% loss or was sacrificed due to >20% loss. Mice were also terminated when hind-limb paralysis developed or if they became otherwise moribund.

Figure 11:
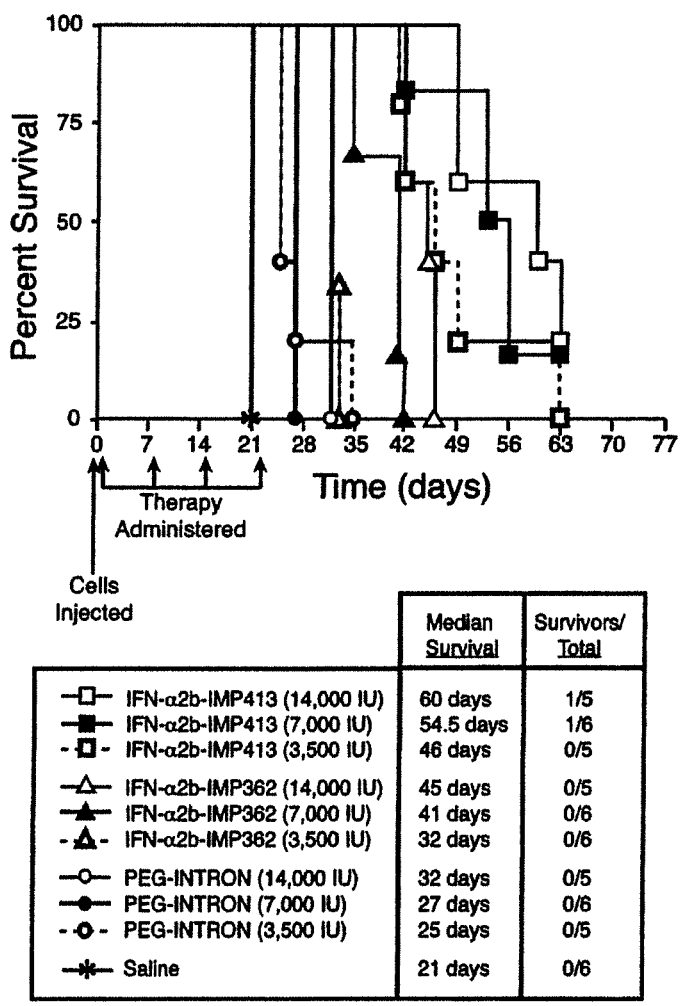
FIG. 11. Evaluation of the therapeutic efficacy of IFNα constructs in mice bearing Burkitt's lymphoma (Daudi). Eight-week-old female SCID mice were injected i.v. with $1.5 \times 10^7$ Daudi cells. Groups of 5 mice were administered PEGINTRON™, α2b-362 and α2b-413 at doses of 3,500, 7,000 or 14,000 Units once per week for 4 weeks. Therapy commenced 1 day after the Daudi cells were transplanted. Injection times are indicated with arrows. Survival curves and median survival are shown for each group.

Survival curves generated from this study are shown in FIG. 11. PEGINTRON™, α2b-362, and α2b-413 all demonstrated significant improvement in survival when compared to saline control mice (P<0.0016). Except for the 3,500 IU dose of α2b-362, both α2b-413 and α2b-362 were superior to PEGINTRON™ when administered at equal activity doses (P≤0.0027). α2b-362 showed more than twice the potency of PEGINTRON™. Doses of 7,000 IU and 3,500 IU of α2b-362 were superior to 14,000 IU (P=0.0016) and 7,000 IU (P=0.0027) doses of PEGINTRON™, respectively. α2b-413 is more than four times as potent as PEGINTRON™since a 3,500 IU dose of the former was superior to 14,000 IU of the latter (P=0.0027). α2b-413 was significantly better than α2b-362 (P<0.0025) when administered at equivalent doses. However, there were no statistically significant differences among the three doses of α2b-413, even though the 14,000 IU dose resulted in a median survival of 60 days in comparison to the 3,500 IU dose and its 46-day median survival (P=0.1255). The in vivo efficacy observed for α2b-362, α2b-413, and PEGINTRON™ thus correlate well with the PK data.

The increased bioavailability of α2b-362 and α2b-413 demonstrated by PK analysis contributes to the enhanced in vivo anti-tumor potency of DNL-PEGylated IFNα. In turn, these two factors allow for a less frequent dosing schedule used in tumor therapy. This was demonstrated with a similar in vivo tumor therapy study as above, in which equal units of activity of PEGINTRON™ or α2b-413 were administered with varied dosing schedules. This study was performed in 8-week-old female SCID mice injected i.v. with Daudi $1.5 \times 10^7$ cells. There were 7 different treatment groups of 6-7 mice each. Each reagent (test and control) was administered 14,000 IU via a s.c. injection in either the left or right flank. Therapy was commenced 1 day after the Daudi-cells were administered to the mice. One set of mice was dosed once a week for 4 weeks (q7d×4), another dosed on a bi-weekly schedule over 8 weeks (q2wk×4), while the third set of mice was dosed once every 3 weeks over 12 weeks (q3wk×4). All the mice received a total of 4 injections.

Figure 12:
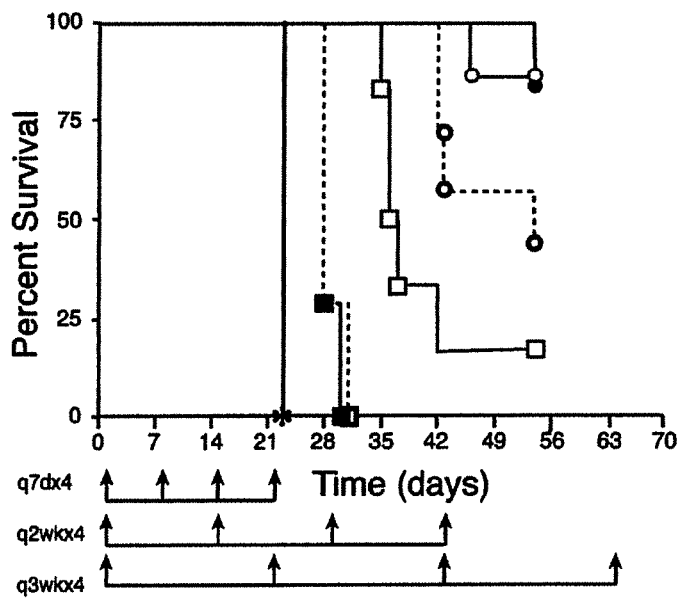
FIG. 12. Evaluation of the dosing schedule for therapy of tumor-bearing mice. Eight-week-old female SCID mice were injected i.v. with $1.5 \times 10^7$ Daudi-cells. Groups of 6-7 mice were administered 14,000 IU of either PEGINTRON™ or α2b-413 via a s.c. injection. Therapy was commenced 1 day after the Daudi cells were administered to the mice. Groups were dosed once a week (q7d×4), once every other week (q2wk×4) or once every 3 weeks (q3wk×4). Injection times are indicated with arrows. All the mice received 4 injections in total. Survival curves and median survival are shown for each group.

Survival curves generated from this study are shown in FIG. 12. All animals that received either form of interferon at any of the various schedules had significantly improved survival in comparison to saline control mice (P<0.0009). Importantly, all the IFN-IMP413-treated mice had significantly improved survival when compared to those animals treated at the same schedule with PEGINTRON™ (P<0.0097). Of note, those mice treated every other week with IFN-1MP413 (q2wk×4) not only had significantly improved survival in comparison to those treated with PEGINTRON™ at the same schedule (MST=>54 days versus 28 days, respectively; P=0.0002), but were also significantly better than those animals treated weekly (q7d×4) with PEGINTRON™ (MST=36.5 days; P=0.0049). Further, survival of mice treated every three weeks with IFN-IMP413 (q3wk×4) was significantly better than those treated with PEGINTRON™ every two weeks (MST=54 days versus 28 days; P=0.002) and approaches significance when compared to those treated weekly with PEGINTRON™ (P=0.0598).

These studies demonstrate DNL-PEGylation of IFNα2b results in improved and long-lasting efficacy, allowing for less frequent dosing. Similar enhancements is realized when this technology is applied to other cytokines (such as G-CSF and EPO), growth factors, enzymes, antibodies, immunomodulators, hormones, peptides, drugs, interference RNA, oligonucleotides, vaccines and other biologically active agents.

Example 6

Generation of DDD Module Based on Granulocyte-Colony Stimulating Factor (G-CSF)

Construction of G-CSF-DDD2-pdHL2 for Expression in Mammalian Cells

The cDNA sequence for G-CSF was amplified by PCR resulting in sequences comprising the following features, in which XbaI and BamHI are restriction sites, the signal peptide is native to human G-CSF, and 6 His is a hexahistidine tag (SEQ ID NO: 10): XbaI---Signal peptide---G-CSF---6 His---BamHI ("6 His" disclosed as SEQ ID NO: 10). The resulting secreted protein consisted of G-CSF fused at its C-terminus to a polypeptide consisting of SEQ ID NO:5.

(SEQ ID NO: 2)
KSHHHHHHGSGGGGSGGGCGHIQIPPGLTELLQGYTVEVLRQQPPDLVEF

AVEYFTRLREARA

PCR amplification was accomplished using a full-length human G-CSF cDNA clone (Invitrogen IMAGE human cat#97002RG Clone ID 5759022) as a template and the following oligonucleotides as primers:

G-CSF XbaI Left
(SEQ ID NO: 5)
5'-TCTAGACACAGGACCTCATCATGGCTGGACCTGCCACCCAG-3'

G-CSF BamHI-Right
(SEQ ID NO: 6)
5'-GGATCCATGATGGTGATGATGGTGTGACTTGGGCTGGGCAAGGTGGC

GTAG-3'

The PCR amplimer was cloned into the pGemT vector. A DDD2-pdHL2 mammalian expression vector was prepared for ligation with G-CSF by digestion with XbaI and Bam HI restriction endonucleases. The G-CSF amplimer was excised from pGemT with XbaI and Bam HI and ligated into the DDD2-pdHL2 vector to generate the expression vector G-CSF-DDD2-pdHL2.

Mammalian Expression of G-CSF-DDD2

G-CSF-pdHL2 was linearized by digestion with SalI enzyme and stably transfected into Sp/EEE myeloma cells by electroporation. Clones were selected with media containing 0.15 µM MTX. Clone #4 was shown to produce 0.15 mg/L of G-CSF-DDD2 by sandwich ELISA.

Purification of G-CSF-DDD2 from Batch Cultures Grown in Roller Bottles

Approximately 3 mg of G-CSF-DDD2 is purified as descried in Example 2. Clone 4 is expanded to 34 roller bottles containing a total of 20 L of Hybridoma SFM with 0.4 µM MTX and allowed to reach terminal culture. The supernatant fluid is clarified by centrifugation, filtered (0.2 µM), diafiltered into 1× Binding buffer (10 mM Imidazole, 0.5 M NaCl, 50 mM $NaH_2PO_4$, pH 7.5 and concentrated. The concentrate is loaded onto a Ni-NTA column, which is washed with 0.02% Tween 20 in 1× binding buffer and then 30 mM imidazole, 0.02% Tween 20, 0.5 M NaCl, 50 mM $NaH_2PO_4$, pH 7.5. The product is eluted with 250 mM imidazole, 0.02% Tween 20, 150 mM NaCl, 50 mM $NaH_2PO_4$, pH 7.5.

Example 7

Generation of PEGylated G-CSF by DNL

Figure 13:
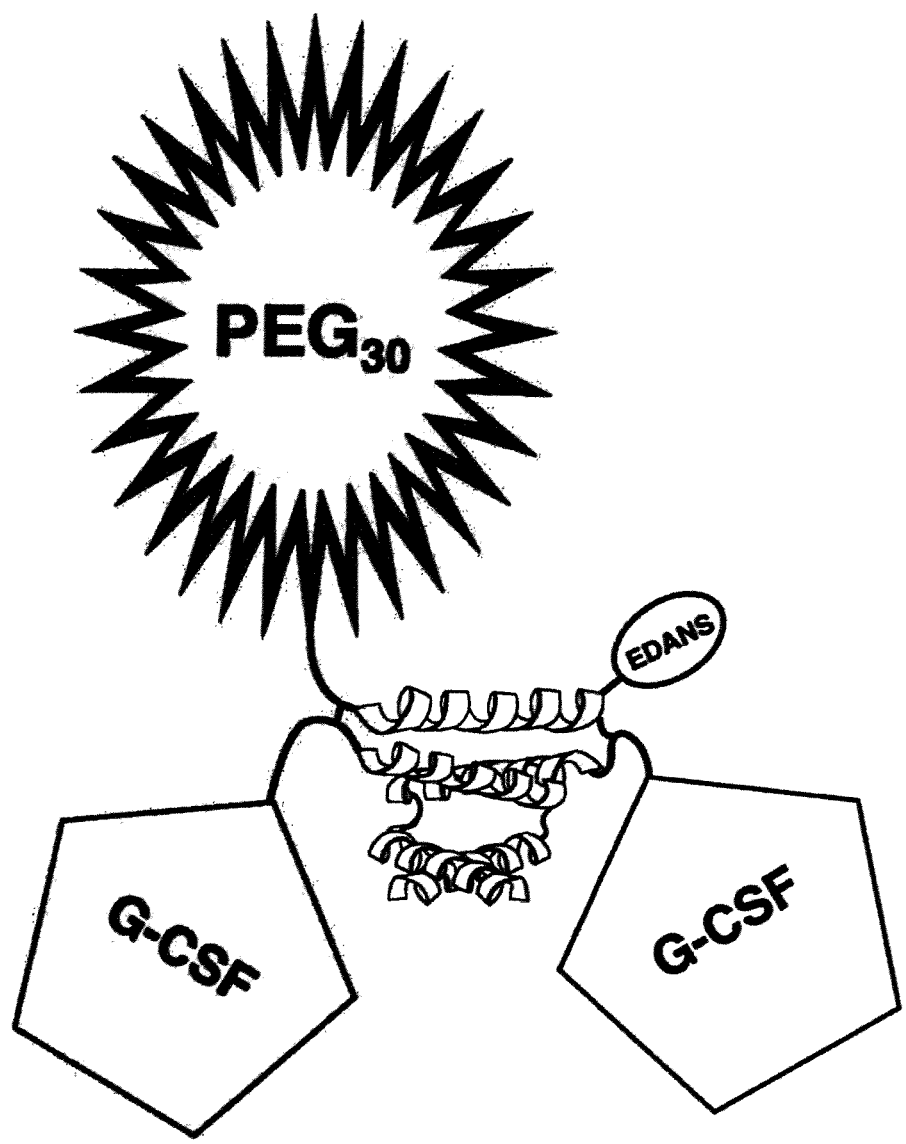
FIG. 13. Cartoon drawing of G-CSF-413. G-CSF groups (pentagons), 30 kDa PEG (starburst), AD2 and DDD2 peptides (helices) and EDANS fluorescent tag (oval) are indicted.

A cartoon drawing depicting the structure of G-CSF-413 having two copies of G-CSF coupled to a 30 kDa PEG is provided in FIG. 13. A DNL reaction is performed by the addition of reduced and lyophilized IMP413 in 10-fold molar excess to G-CSF-DDD2 in PBS. After 6 h at room temperature in the dark, the reaction mixture is purified by immobilized metal affinity chromatography using Ni-NTA.

Example 8

Generation of DDD Module Based on Erythropoeitin (EPO)

Construction of G-CSF-DDD2-pdHL2 for Expression in Mammalian Cells

The cDNA sequence for EPO was amplified by PCR resulting in sequences comprising the following features, in which XbaI and BamHI are restriction sites, the signal peptide is native to human EPO, and 6 His is a hexahistidine tag (SEQ ID NO: 10): XbaI---Signal peptide---EPO---6 His---BamHI ("6 His" disclosed as SEQ ID NO: 10). The resulting secreted protein consists of EPO fused at its C-terminus to a polypeptide consisting of SEQ ID NO:2.

PCR amplification was accomplished using a full-length human EPO cDNA clone as a template and the following oligonucleotides as primers:

EPO Xba I left
(SEQ ID NO: 7)
5'-TCTAGACACAGGACCTCATCATGGGGGTGCACGAATGTCC-3'

EPO BamHI Right
(SEQ ID NO: 8)
5'-GGATCCATGATGGTGATGATGGTGTGACTTTCTGTCCCCTGTCCTGC

AG-3'

The PCR amplimer was cloned into the pGemT vector. A DDD2-pdHL2 mammalian expression vector was prepared for ligation with EPO by digestion with XbaI and Bam HI restriction endonucleases. The EPO amplimer was excised from pGemT with XbaI and Bam HI and ligated into the DDD2-pdHL2 vector to generate the expression vector EPO-DDD2-pdHL2.

Mammalian Expression of EPO-DDD2

EPO-pdHL2 was linearized by digestion with SalI enzyme and stably transfected into Sp/EEE myeloma cells by electroporation. Clones were selected with media containing 0.15 µM MTX. Clones #41, 49 and 37 each were shown to produce ~0.5 mg/L of EPO by an ELISA using Nunc Immobilizer Nickel-Chelate plates to capture the His-tagged fusion protein and detection with anti-EPO antibody.

Purification of EPO from Batch Cultures Grown in Roller Bottles

Figure 14:
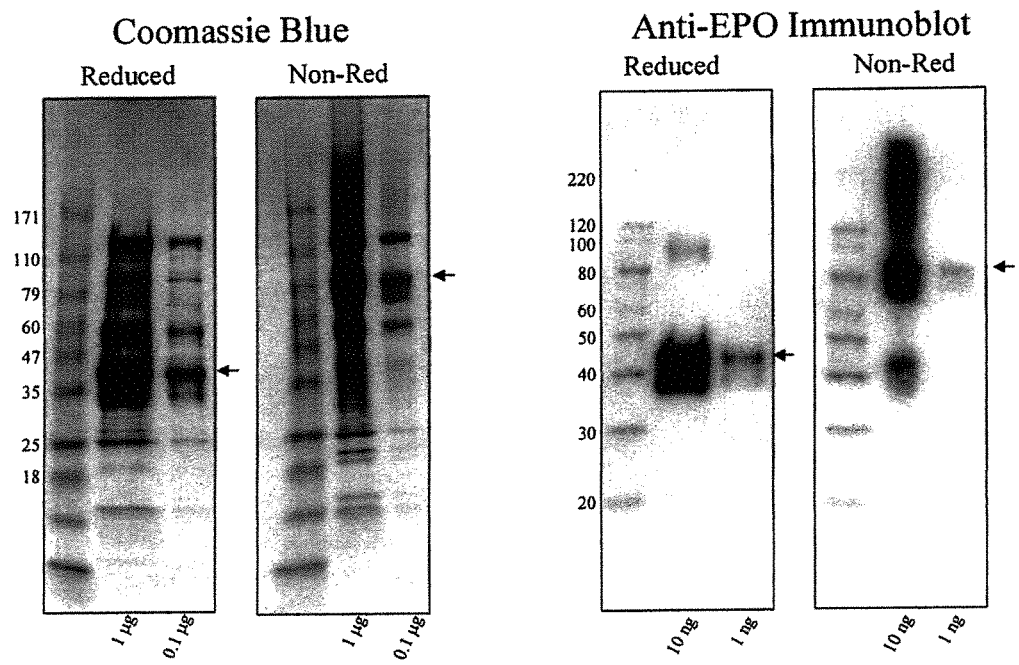
FIG. 14. SDS-PAGE and anti-EPO immunoblot analysis of IMAC-purified EPO-DDD2. Proteins were resolved by SDS-PAGE under reducing or non-reducing conditions and gels were stained with Coomassie blue or transferred to PVDF membranes for immunoblot analysis with an anti-EPO monoclonal antibody. The amounts of protein loaded/lane is indicated at the bottom of the lanes. The positions of MW standards and of EPO-DDD2 (arrow) are indicated.

Approximately 2.5 mg of EPO-DDD2 is purified by IMAC from 9.6 liters of serum-free roller bottle culture as described in Example 2. SDS-PAGE and immunoblot analysis indicate that the purified product constitutes approximately 10% of the total protein following IMAC (FIG. 14). Under reducing conditions the EPO-DDD2 polypeptide is resolved as a broad band with a $M_r$ (40-45 kDa) greater than its calculated mass (28 kDa) due to extensive and heterogeneous glycosylation. Under non-reducing conditions the EPO-DDD2 primarily resolves as a disulfide-linked covalent dimer (mediated by DDD2) with a $M_r$ of 80-90 kDa.

Example 9

Figure 15:
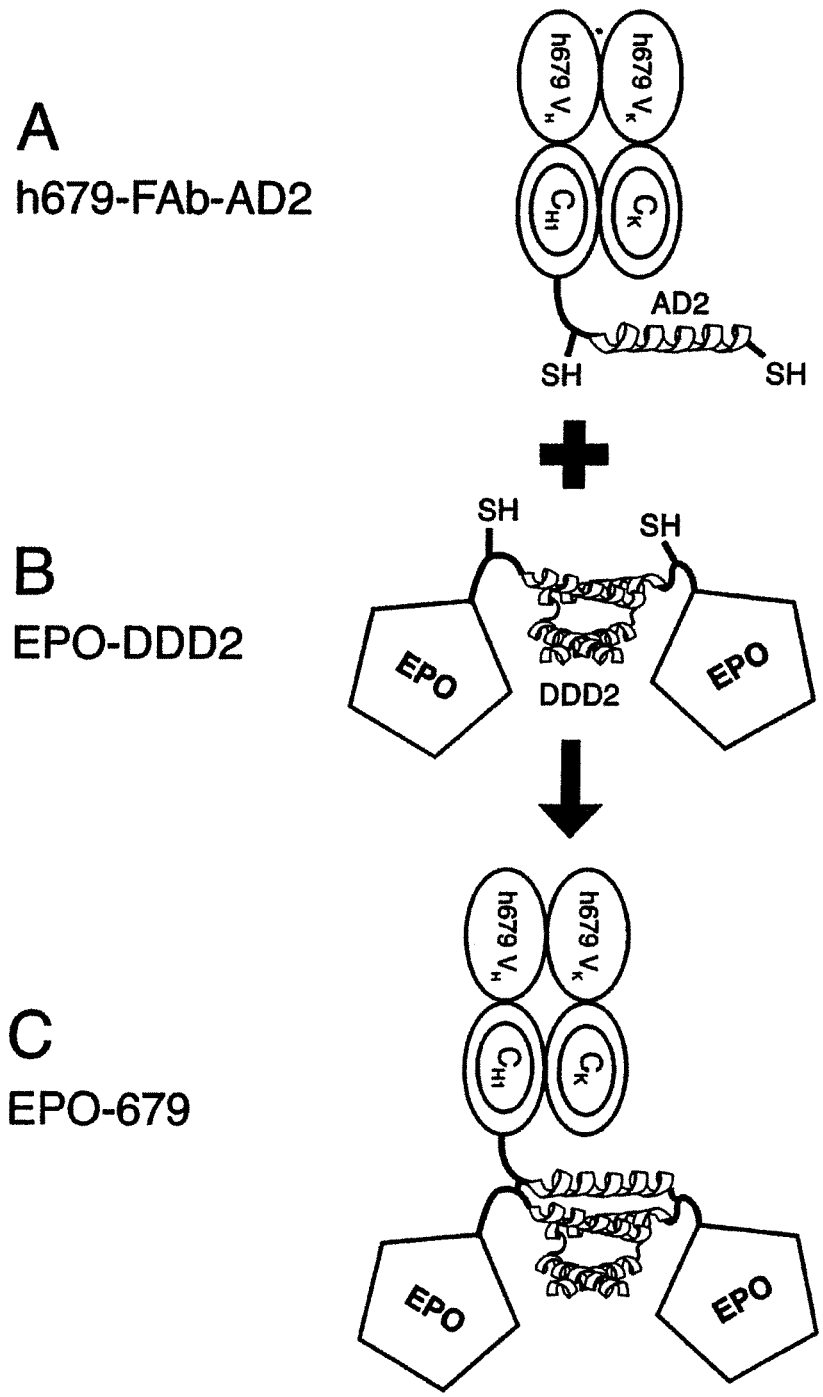
FIG. 15. Cartoon drawings of h679-Fab-DDD2 (A), dimeric EPO-DDD2 (B), which combine to create EPO-679 (C) by the DNL method. The variable and constant domains of h679 Fab (ovals), AD2 and DDD2 helices, EPO groups (pentagons) and free sulfhydryl groups (SH) are indicated.
Figure 16:
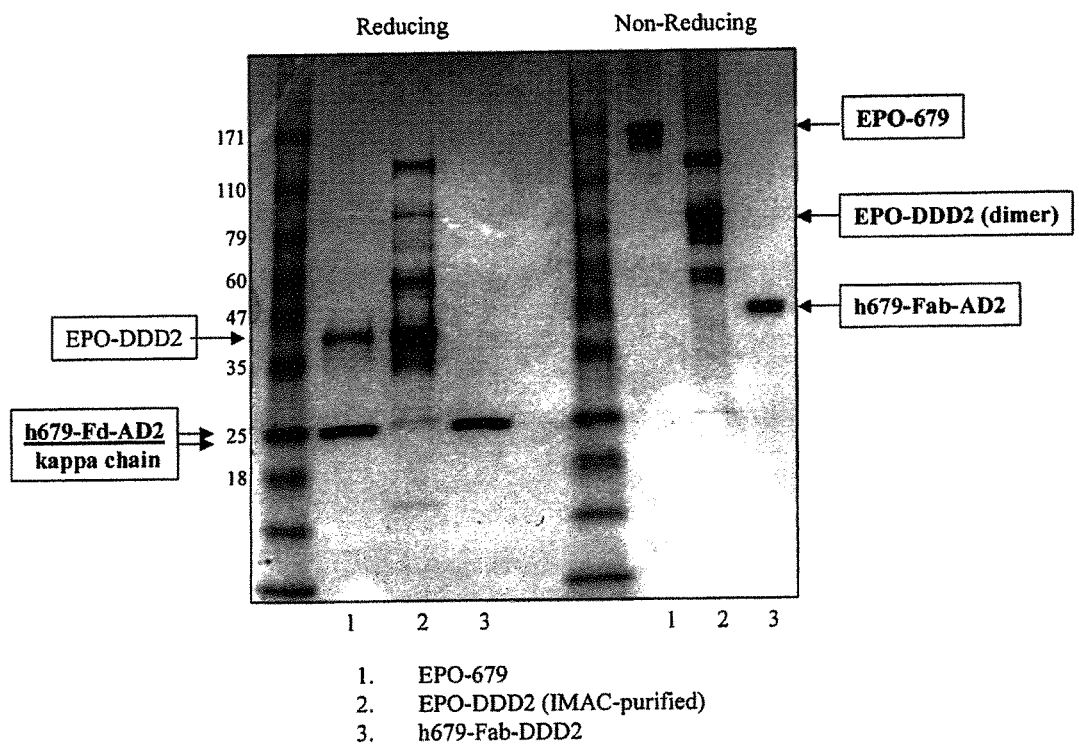
FIG. 16. SDS-PAGE analysis of EPO-679. Proteins (1 μg) were resolved by SDS-PAGE under reducing and non-reducing conditions in the lanes as indicated and gels were stained with Coomassie blue. The positions of MW standards and all relevant species (arrows) are indicated.

DNL Conjugation of EPO-DDD2 with a Fab-AD2 Module h679 is a humanized monoclonal antibody that is highly specific for the hapten HSG (histamine-succinyl-glycine). Production of an h679-Fab-AD2 module, which is depicted in the cartoon drawing in FIG. 15 (A), has been described previously (Rossi et. al, Proc. Natl. Acad. Sci. USA. 2006; 103:6841). A cartoon drawing depicting the dimeric structure of EPO-DDD2 is provided in FIG. 15 (B). A small-scale preparation of EPO-679 (EPO-DDD2×h679-Fab-AD2) was made by DNL. EPO-DDD2 (1 mg) was reacted overnight with h679-Fab-AD2 (1 mg) in PBS containing 1 mM reduced glutathione and 2 mM oxidized glutathione. The DNL conjugate was purified by HSG-based affinity chromatography as described previously (Rossi et. al, Proc. Natl. Acad. Sci. USA. 2006; 103:6841). A cartoon drawing depicting the structure of EPO-679 with two EPO moieties and h679-Fab is provided in FIG. 15 (C). Coomassie blue staining of SDS-PAGE gels demonstrated the creation of EPO-679 (FIG. 16). The DNL product, which is resolved as a broad band with a $M_r$ of 150-170 kDa under non-reducing conditions, is highly purified and consists only of the three constituent polypeptides (EPO, h679-Fd-AD2 and h679 Kappa) as demonstrated by SDS-PAGE under reducing conditions.

Example 10

Biological Activity of EPO-DDD2 and EPO-679

Figure 17:
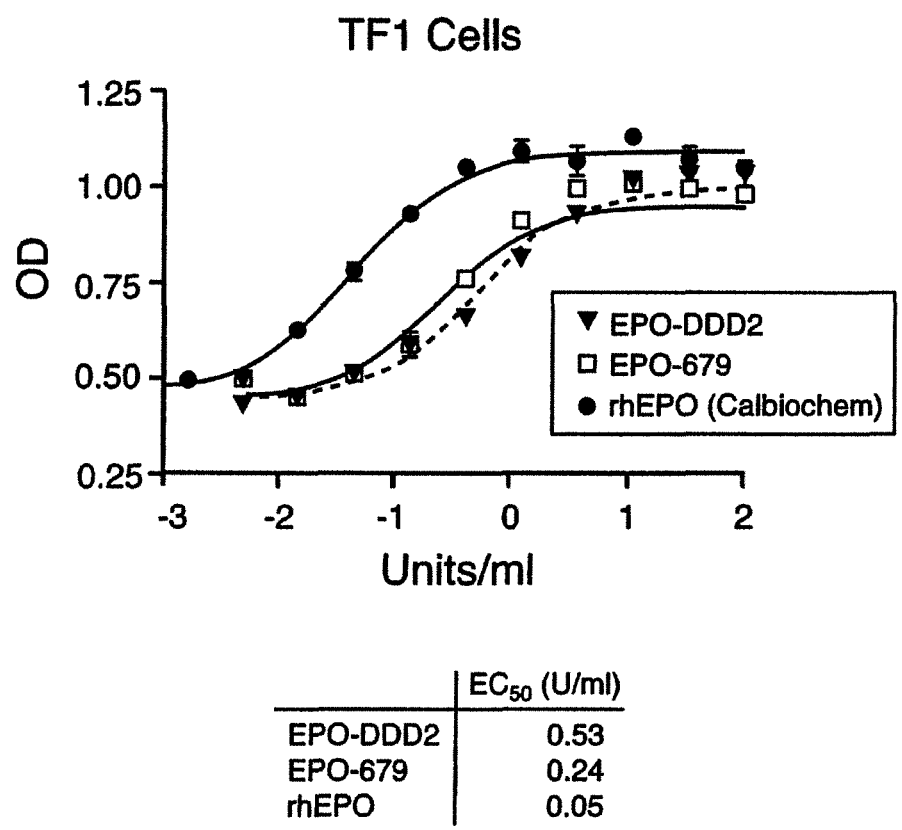
FIG. 17. Stimulation of cell growth by EPO-constructs. EPO-responsive TF1 cells ($1 \times 10^4$) were cultured for 72 hours in the presence of rhEPO, EPO-DDD2 or EPO-679. The relative viable cell density was determined by MTS assay. The log of the concentration in U/mL is plotted vs. $OD_{490}$.

EPO-DDD2 and EPO-679 were assayed for their ability to stimulate the growth of EPO-responsive TF1 cells (ATCC) using recombinant human EPO (Calbiochem) as a positive control. TF1 cells were grown in RPMI 1640 media supplemented with 20% FBS without GM-CSF supplementation in 96-well plates containing $1 \times 10^4$ cells/well. The concentrations (units/ml) of the EPO constructs were determined using a commercial kit (Human erythropoietin ELISA kit, Stem Cell Research, Cat#01630). Cells were cultured in the presence of rhEPO, EPO-DDD2 or EPO-679 at concentrations ranging from 900 U/ml to 0.001 U/ml for 72 hours. The viable cell densities were compared by MTS assay using 20 µl of MTS reagent/well incubated for 6 hours before measuring the OD490 in a 96-well plate reader. Dose response curves and EC50 values were generated using Graph Pad Prism software (FIG. 17). Both EPO-DDD2 and EPO-679 show in vitro biological activity at approximately 10% of the potency of rhEPO.

Example 11

Generation of PEGylated EPO by DNL

Figure 18:
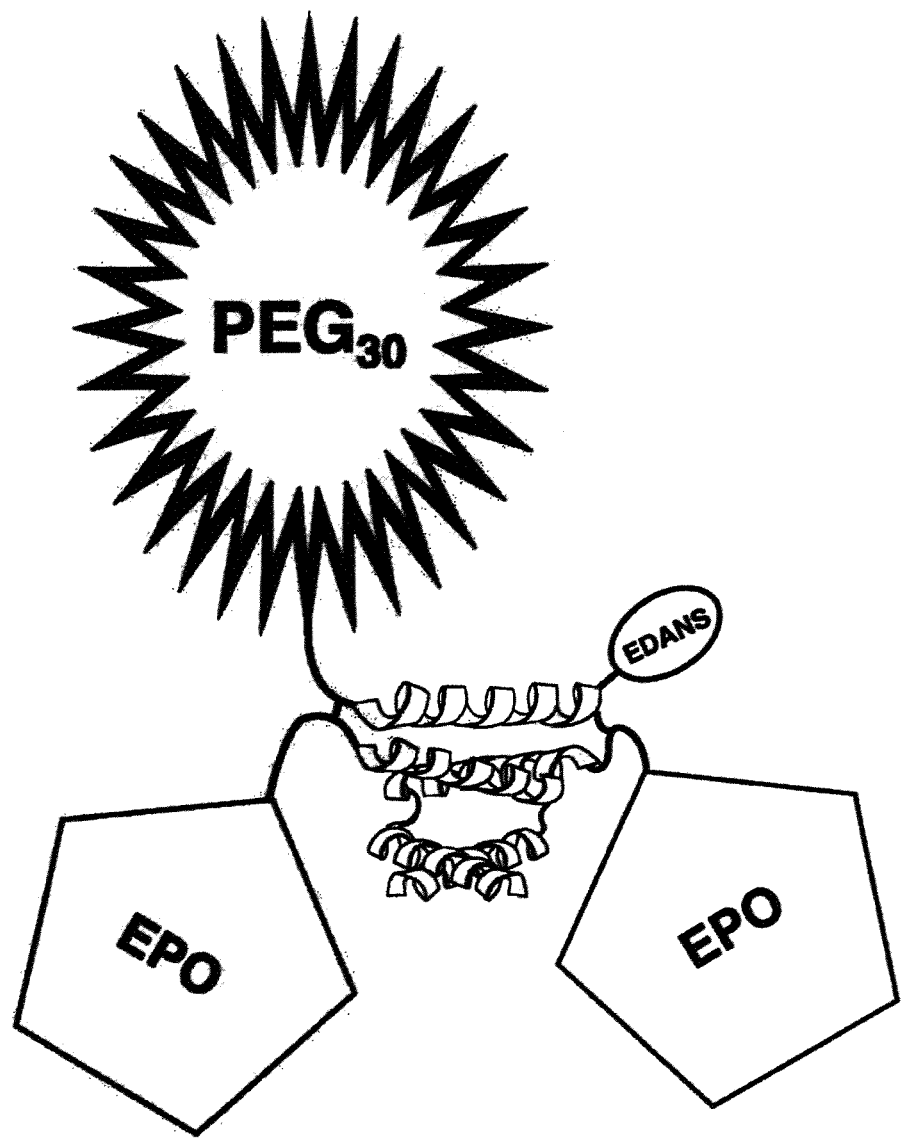
FIG. 18. Cartoon drawing of EPO-413. EPO groups (pentagons), 30 kDa PEG (starburst), AD2 and DDD2 peptides (helices) and EDANS fluorescent tag (oval) are indicted.

A cartoon drawing depicting the structure of EPO-413 having two copies of EPO coupled to a 30 kDa PEG is provided in FIG. 18. A DNL reaction is performed by the addition of reduced and lyophilized IMP413 in 10-fold molar excess to EPO-DDD2 in PBS. After 6 h at room temperature in the dark, the reaction mixture is purified by immobilized metal affinity chromatography using Ni-NTA.

Example 12

Production of 2-PEG:1-Target Agent Complexes

In alternative embodiments, it is desirable to make PEGylated complexes with a stoichiometry of 2 PEG moieties to 1 target agent. Such PEGylated complexes are readily made by the methods of Examples 1-3 above, by attaching the PEG moiety to the DDD sequence and the active agent to the AD sequence. A PEGylated complex with a 2:1 stoichiometry of PEG to IFN-α2b is prepared by a modification of the methods of Examples 1-3. The complex exhibits stability in serum and shows interferon activity that is lower than the PEGylated complex with a 1:2 stoichiometry of PEG to IFN-α2b. However, clearance rate for the bi-PEGylated complex is slower than the clearance rate for the mono-PEGylated complex.

What is claimed is:

1. A PEGylated complex comprising:
   a) a therapeutic agent attached to a DDD (dimerization and docking domain) moiety, wherein the amino acid sequence of the DDD moiety consists of the N-terminal 44 amino acids from human protein kinase A (PKA) RIIα; and
   b) a PEG moiety attached to an AD (anchor domain) moiety wherein the amino acid sequence of the AD moiety is from an AKAP protein;
   wherein two copies of the DDD sequences bind to one copy of the AD sequence to form a PEGylated complex.

2. The complex of claim 1, wherein the amino acid sequence of the AD moiety is selected from the group consisting of SEQ ID NO:1.

3. The complex of claim 1, further comprising disulfide bonds between the DDD and AD moieties.

4. The complex of claim 1, wherein the therapeutic agent is selected from the group consisting of an enzyme, a cytokine, a chemokine, a growth factor, an antibody and an antigen binding fragment thereof.

5. The complex of claim 1, wherein the therapeutic agent is selected from the group consisting of interferon-α, interferon-β, interferon-γ, MIF, HMGB-1 (high mobility group box protein 1), TNF-α, G-CSF and GM-CSF.

6. The complex of claim 1, wherein the complex comprises a structure selected from the group consisting of: (i) IMP350: CGQIEYLAKQIVDNAIQQAGC(SS-tbu) -NH$_2$ (SEQ ID NO:1), (ii) IMP360: CGQIEYLAKQIVDNAIQQAGC(SS-tbu)G-EDANS (SEQ ID NO:1), (iii) IMP362: PEG$_{20}$-CGQIEYLAKQIVDNAIQQAGC(SS-tbu)G-EDANS (SEQ ID NO:1); and (iv) IMP413: PEG$_{30}$-CGQ-IEYLAKQIVDNAIQQAGC(SS-tbu) G-EDANS (SEQ ID NO:1).

7. The complex of claim 1, wherein the therapeutic agent is a cytokine.

8. The complex of claim 1, wherein the therapeutic agent is interferon (IFN)-α, G-CSF or erythropoietin.

9. The complex of claim 1, wherein the therapeutic agent attached to the DDD sequence is a fusion protein.

10. The complex of claim 1, wherein the complex comprises one PEG moiety and two therapeutic agents.

11. The complex of claim 1, wherein the therapeutic agent is selected from the group consisting of IL-1, IL-2, IL-3, IL-4, IL-5, IL-6, IL-7, IL-8, IL-9, IL-10, IL-11, IL-12, IL-13, IL-15, IL-16, IL-17, and IL-18.

12. The complex of claim 1, wherein the therapeutic agent is selected from the group consisting of Eotaxin, CCL19, CCL21, RANTES, MIP-1A, MIP-1B, ENA-78, MCP-1, IP-10, and Gro-β.

13. The complex of claim 1, wherein the therapeutic agent is selected from the group consisting of PDGF, Flt-3 ligand, erythropoietin, thrombopoietin, hGH, CNTF, VEGF, P1GF, insulin, IGF, somatostatin, tissue plasminogen activator, and LIF.

* * * * *

SEQUENCE LISTING

```
<160> NUMBER OF SEQ ID NOS: 10

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 2
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Ser His His His His His His Gly Ser Gly Gly Gly Gly Ser Gly
1               5                   10                  15
```

-continued

Gly Gly Cys Gly His Ile Gln Ile Pro Pro Gly Leu Thr Glu Leu Leu
                20                  25                  30

Gln Gly Tyr Thr Val Glu Val Leu Arg Gln Gln Pro Pro Asp Leu Val
        35                  40                  45

Glu Phe Ala Val Glu Tyr Phe Thr Arg Leu Arg Glu Ala Arg Ala
    50                  55                  60

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctagacaca ggacctcatc atggccttga cctttgcttt actgg                45

<210> SEQ ID NO 4
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggatccatga tggtgatgat ggtgtgactt ttccttactt cttaaacttt cttgc        55

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tctagacaca ggacctcatc atggctggac ctgccaccca g                      41

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatccatga tggtgatgat ggtgtgactt gggctgggca aggtggcgta g            51

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctagacaca ggacctcatc atgggggtgc acgaatgtcc                        40

<210> SEQ ID NO 8
<211> LENGTH: 49
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 8
ggatccatga tggtgatgat ggtgtgactt tctgtcccct gtcctgcag                49

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Gly Gln Ile Glu Tyr Leu Ala Lys Gln Ile Val Asp Asn Ala Ile
1               5                   10                  15

Gln Gln Ala Gly Cys Gly
            20

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5
```